US007723048B2

(12) United States Patent
Bilsborough et al.

(10) Patent No.: US 7,723,048 B2
(45) Date of Patent: May 25, 2010

(54) METHODS OF PREDICTING THERAPEUTIC RESPONSE IN ATOPIC DERMATITIS TO IL-31 ANTAGONISTS

(75) Inventors: Janine Bilsborough, Seattle, WA (US); Jane A. Gross, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/239,107

(22) Filed: Sep. 26, 2008

(65) Prior Publication Data

US 2009/0092999 A1 Apr. 9, 2009

Related U.S. Application Data

(62) Division of application No. 11/353,454, filed on Feb. 14, 2006, now abandoned.

(60) Provisional application No. 60/653,114, filed on Feb. 14, 2005, provisional application No. 60/716,762, filed on Sep. 13, 2005, provisional application No. 60/749,952, filed on Dec. 13, 2005.

(51) Int. Cl.
*G01N 33/00* (2006.01)
*G01N 33/53* (2006.01)
(52) U.S. Cl. ..................................................... 435/7.1
(58) Field of Classification Search ....................... None
See application file for complete search history.

(56) References Cited

U.S. PATENT DOCUMENTS

| 5,925,735 | A | 7/1999 | Baumgartner et al. |
| 7,064,186 | B2 * | 6/2006 | Sprecher et al. ............. 530/351 |
| 2003/0215838 | A1 | 11/2003 | Sprecher et al. |
| 2003/0224487 | A1 * | 12/2003 | Sprecher et al. ............ 435/69.5 |
| 2006/0141579 | A1 | 6/2006 | Sprecher et al. |
| 2006/0182743 | A1 | 8/2006 | Bilsborough |
| 2006/0188499 | A1 | 8/2006 | Leung et al. |
| 2006/0188500 | A1 | 8/2006 | Leung et al. |
| 2006/0228329 | A1 | 10/2006 | Brady et al. |
| 2006/0275296 | A1 | 12/2006 | Siadak et al. |
| 2007/0077627 | A1 | 4/2007 | Sprecher et al. |
| 2007/0111266 | A1 | 5/2007 | Sprecher et al. |
| 2007/0160610 | A1 | 7/2007 | Yao et al. |
| 2007/0249020 | A1 | 10/2007 | Sprecher et al. |
| 2008/0260686 | A1 | 10/2008 | Bilsborough et al. |

FOREIGN PATENT DOCUMENTS

| WO | 03/060090 | 7/2003 |
| WO | WO 03060090 A2 * | 7/2003 |
| WO | 2006/081573 | 8/2006 |
| WO | 2006/122079 | 11/2006 |
| WO | 2008/028192 | 3/2008 |

OTHER PUBLICATIONS

Neis et al., "Enhanced expression levels of IL-31 correlate with IL-4 and IL-13 in atopic and allergic contact dermatitis," Journal of Allergy and Clinical Immunology, 118(4): 930-937, Oct. 1, 2006.
Riken, 1999, (GenBank Acc. No. AV040649).
Riken, 1999, (GenBank Acc. No. AV044404).
Riken, 1999, (GenBank Acc. No. AV268991).
Riken, 1999, (GenBank Acc. No. AV280874).
National Cancer Institute, 1997, (GenBank Acc. No. BF152807).
Riken, 2001, (GenBank Acc. No. BB610257).
Riken, Accession No. AK005939, 1999.
Riken, Accession No. AK005939, Jul. 5, 2001.
National Institutes of Health, 1999, (GenBank Acc. No. CA464033).
Riken, 2002, (GenBank Acc. No. BY706076).
Washington University School of Medicine, 2002, (GenBank Acc. No. CF105870).
RZPD Deutsches Ressourcenzentrum fuer Genomforschung GmbH, 2003, (GenBank Acc. No. BX639332).
Whitehead Institute for Biomedical Research, Mouse Public Genomic Sequence TDB 3482986, Jan. 11, 2001.
Washington University Genome Sequencing Center, Mouse Public Genomic Sequence TDB 16727183, Feb. 24, 2001.
Whitehead Institute for Biomedical Research, Mouse Public Genomic Sequence TDB 10456006, Mar. 14, 2001.
Washington University Genome Sequencing Center, Mouse Public Genomic Sequence TDB 8480322, Jan. 13, 2001.
Whitehead Institute for Biomedical Research, Mouse Public Genomic Sequence TDB 49775248, Oct. 5, 2001.
Whitehead Institute for Biomedical Research, Mouse Public Genomic Sequence TDB 10005090, Mar. 10, 2001.
Whitehead Institute for Biomedical Research, Mouse Public Genomic Sequence TDB 20965871, Mar. 16, 2001.
Whitehead Institute for Biomedical Research, Mouse Public Genomic Sequence TDB 44835892, Sep. 20, 2001.
Washington University Genome Sequencing Center, Mouse Public Genomic Sequence TDB 50734527, Oct. 6, 2001.
Sanger Center, Mouse Public Genomic Sequence TDB 40505897, Aug. 31, 2001.
Sanger Center, Mouse Public Genomic Sequence TDB 1021719, Jan. 4, 2001.
Washington University Genome Sequencing Center, Mouse Public Genomic Sequence TDB 22973884, Apr. 16, 2001.
Abstract from The American Society of Human Genetics Meeting, Nov. 7, 2003 on Gene Structure and Function.
EMBL Accession No. AC048338, Apr. 2000.
EMBL Accession No. AA381907, Apr. 1997.

(Continued)

*Primary Examiner*—Cherie M Woodward
(74) *Attorney, Agent, or Firm*—Robyn Adams

(57) ABSTRACT

The present invention relates to predicting therapeutic response of treating patients suffering from itching and puritis mediated by cutaneous lymphocyte antigen positive T cells in atopic dermatitis. The invention also includes methods of predicting a therapeutically responsive patient population.

4 Claims, No Drawings

OTHER PUBLICATIONS

Dillon et al., "Interleukin 31, a cytokine produced by activated T cells, induces dermatitis in mice," Nature Immunology 5(7):752-760, Jul. 2004.

Bilsborough et al., "IL-31 is associated with cutaneous lymphocyte antigen-positive skin homing T-cells in patients with atopic dermatitis", Journal of Allergy and Clinical Immunology, Mosby—Yearly Book, Inc., US 117(2): 418-425, Feb. 7, 2006.

Sonkoly et al., "IL-31: A new link between t-cells and pruritus in atopic skin inflammation", Journal of Allergy and Clinical Immunology, Mosby—Yearly Book, Inc., US 117(2): 411-417, Feb. 2006.

Takaoka et al., "Involvement of IL-31 on scratching behavior in NC/Nga mice with atopic-like dermatitis", Experimental Dermatology, 15 (3): 161-167, Mar. 2006.

Takaoka et al., "Expression of IL-31 gene transcript in NC/Nga mice with atopic dermatitis", European Journal of Pharmacology, Amsterdam, NL, 516 (2): 180-181, May 31, 2005.

Goding, Journal of Immunological Methods vol. 39: 285-308, 1980.

Brune et al., Hautarzt 55: 1130-1136, 2004, abstract only.

Claudy, Pathologie et Biologie, L'Expansion Scientifique Francaise, Paris, FR 44(10): 888-894, 1996, abstract only.

Leung et al., "New insights into atopic dermititis", Journal of Clinical Investigation 113(5): 651-657, Mar. 2004.

Boguniewics et al., "Atopic dermititis", J Allergy Clin Immunol, 117(2): S475-S480, Feb. 2006.

Castellani et al., "Interleukin-31: A new cytokine involved in inflammation of the skin", International Journal of Immunopathology and Pharmacology, 19(1): 1-4, Jan. 13, 2006.

"Monoclonal Anti-human IL-31 Antibody", R&D Systems, Inc., Apr. 18, 2006.

Presta et al., "Engineering of therapeutic antibodies to minimize immunogenicity and optimize function," Advanced Drug Delivery Reviews 58(5-6): 640-656, 2006.

Conti et al., "Modulation of autoimmunity by the latest interleukins (with special emphasis on IL-32)" Autoimmunity Reviews 6(3): 131-137, 2007.

EMBL Accession No. AK005939, Feb. 8, 2001.

Wills-Karp, M., "The gene encoding inerleukin-13: a susceptibility locus for asthma and related traits," Respiratory Research, 1(1): 19-23, Jul. 17, 2000.

Siadak et al., U.S. Appl. No. 11/850,006, filed Sep. 4, 2007.

Sprecher et al., U.S. Appl. No. 12/193,665, filed Aug. 18, 2008.

* cited by examiner

SEQUENCE LISTING

<160> NUMBER OF SEQ ID NOS: 10

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)...(519)

<400> SEQUENCE: 1

```
ctgaagctgg ccttgctctc tctcgcc atg gcc tct cac tca ggc ccc tcg acg        54
                                Met Ala Ser His Ser Gly Pro Ser Thr
                                  1               5 tct gtg ctc ttt ctg ttc tgc tgc ctg gga ggc tgg ctg gcc tcc cac        102
Ser Val Leu Phe Leu Phe Cys Cys Leu Gly Gly Trp Leu Ala Ser His
 10              15                  20                  25 acg ttg ccc gtc cgt tta cta cga cca agt gat gat gta cag aaa ata        150
Thr Leu Pro Val Arg Leu Leu Arg Pro Ser Asp Asp Val Gln Lys Ile
                 30                  35                  40 gtc gag gaa tta cag tcc ctc tcg aag atg ctt ttg aaa gat gtg gag        198
Val Glu Glu Leu Gln Ser Leu Ser Lys Met Leu Leu Lys Asp Val Glu
             45                  50                  55 gaa gag aag ggc gtg ctc gtg tcc cag aat tac acg ctg ccg tgt ctc        246
Glu Glu Lys Gly Val Leu Val Ser Gln Asn Tyr Thr Leu Pro Cys Leu
         60                  65                  70 agc cct gac gcc cag ccg cca aac aac atc cac agc cca gcc atc cgg        294
Ser Pro Asp Ala Gln Pro Pro Asn Asn Ile His Ser Pro Ala Ile Arg
     75                  80                  85 gca tat ctc aag aca atc aga cag cta gac aac aaa tct gtt att gat        342
Ala Tyr Leu Lys Thr Ile Arg Gln Leu Asp Asn Lys Ser Val Ile Asp
 90                  95                 100                 105 gag atc ata gag cac ctc gac aaa ctc ata ttt caa gat gca cca gaa        390
Glu Ile Ile Glu His Leu Asp Lys Leu Ile Phe Gln Asp Ala Pro Glu
                110                 115                 120 aca aac att tct gtg cca aca gac acc cat gaa tgt aaa cgc ttc atc        438
Thr Asn Ile Ser Val Pro Thr Asp Thr His Glu Cys Lys Arg Phe Ile
            125                 130                 135 ctg act att tct caa cag ttt tca gag tgc atg gac ctc gca cta aaa        486
Leu Thr Ile Ser Gln Gln Phe Ser Glu Cys Met Asp Leu Ala Leu Lys
        140                 145                 150 tca ttg acc tct gga gcc caa cag gcc acc act taaggccatc tcttcctttc      539
Ser Leu Thr Ser Gly Ala Gln Gln Ala Thr Thr
    155                 160 ggattggcag gaacttaagg agccttaaaa agatgaccga cagctaagtg tgggaactct      599
gccgtgattc cttaagtaca tttttccaat gaataatctc agggacccct catatgggct      659
agtcccggga gggctgagat gtgaatttgt gaattacctt gaaaaacatt aggttattgt      719
tattagtctt ggtatttatg gaatgctttt cctctgcagg cttaagtctt acttattata      779
ccctcgtgag ggtgggaggt ggcagctatg ttaatttatt gatattttatt gtactaagag      839 ttgtcaatgc tccctggggg agccctcgga atctatttaa taaattatat tgaattttc       899
``` tcata                                                                 904

<210> SEQ ID NO 2
<211> LENGTH: 164
<212> TYPE: PRT
<213> ORGANISM: Homo sapiens

<400> SEQUENCE: 2

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Lys Gly Val Leu Val
    50                  55                  60

Ser Gln Asn Tyr Thr Leu Pro Cys Leu Ser Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 3
<211> LENGTH: 755
<212> TYPE: DNA
<213> ORGANISM: Mus musculus
<220> FEATURE:
<221> NAME/KEY: CDS
<222> LOCATION: (1)...(489)

<400> SEQUENCE: 3 atg atc ttc cac aca gga aca acg aag cct acc ctg gtg ctg ctt tgc     48
Met Ile Phe His Thr Gly Thr Thr Lys Pro Thr Leu Val Leu Leu Cys
1               5                   10                  15 tgt ata gga acc tgg ctg gcc acc tgc agc ttg tcc ttc ggt gcc cca     96
Cys Ile Gly Thr Trp Leu Ala Thr Cys Ser Leu Ser Phe Gly Ala Pro
            20                  25                  30 ata tcg aag gaa gac tta aga act aca att gac ctc ttg aaa caa gag    144
Ile Ser Lys Glu Asp Leu Arg Thr Thr Ile Asp Leu Leu Lys Gln Glu
        35                  40                  45 tct cag gat ctt tat aac aac tat agc ata aag cag gca tct ggg atg    192
Ser Gln Asp Leu Tyr Asn Asn Tyr Ser Ile Lys Gln Ala Ser Gly Met
    50                  55                  60 tca gca gac gaa tca ata cag ctg ccg tgt ttc agc ctg gac cgg gaa    240
Ser Ala Asp Glu Ser Ile Gln Leu Pro Cys Phe Ser Leu Asp Arg Glu
65                  70                  75                  80 gca tta acc aac atc tcg gtc atc ata gca cat ctg gag aaa gtc aaa    288
Ala Leu Thr Asn Ile Ser Val Ile Ile Ala His Leu Glu Lys Val Lys
                85                  90                  95 gtg ttg agc gag aac aca gta gat act tct tgg gtg ata aga tgg cta    336

```
Val Leu Ser Glu Asn Thr Val Asp Thr Ser Trp Val Ile Arg Trp Leu
            100                 105                 110 aca aac atc agc tgt ttc aac cca ctg aat tta aac att tct gtg cct    384
Thr Asn Ile Ser Cys Phe Asn Pro Leu Asn Leu Asn Ile Ser Val Pro
        115                 120                 125 gga aat act gat gaa tcc tat gat tgt aaa gtg ttc gtg ctt acg gtt    432
Gly Asn Thr Asp Glu Ser Tyr Asp Cys Lys Val Phe Val Leu Thr Val
130                 135                 140 tta aag cag ttc tca aac tgc atg gca gaa ctg cag gct aag gac aat    480
Leu Lys Gln Phe Ser Asn Cys Met Ala Glu Leu Gln Ala Lys Asp Asn
145                 150                 155                 160 act aca tgc tgagtgatgg ggggggggg ggtgcagtgt cctcagcagt             529
Thr Thr Cys gcctgtcctt cgagggctga gcttgcaacc caggacttaa ctccaaaggg actgtgcggt   589
cattactagt catgttattt atgtttttat tttgtccact gaaatcttgt tctgctaccc   649
tgtagggact ggaagtggca gctatattta tttatttatg tactgagttt gttaacgctc   709
catggaggag ccttcagagt ctatttaata aattatattg acatga                 755

<210> SEQ ID NO 4
<211> LENGTH: 163
<212> TYPE: PRT
<213> ORGANISM: Mus musculus

<400> SEQUENCE: 4

Met Ile Phe His Thr Gly Thr Thr Lys Pro Thr Leu Val Leu Leu Cys
  1               5                  10                  15

Cys Ile Gly Thr Trp Leu Ala Thr Cys Ser Leu Ser Phe Gly Ala Pro
                 20                  25                  30

Ile Ser Lys Glu Asp Leu Arg Thr Ile Asp Leu Leu Lys Gln Glu
             35                  40                  45

Ser Gln Asp Leu Tyr Asn Asn Tyr Ser Ile Lys Gln Ala Ser Gly Met
         50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ala His Leu Glu Lys Val Lys
                 85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
130                 135                 140

Leu Lys Gln Phe Ser Asn Cys Met Ala Glu Leu Gln Ala Lys Asp Asn
145                 150                 155                 160

Thr Thr Cys

<210> SEQ ID NO 5
<211> LENGTH: 1557
<212> TYPE: DNA
<213> ORGANISM: Hiomo sapiens
<220> FEATURE:
<221> NAME/KEY: CDS
<222> LOCATION: (1)...(1557)

<400> SEQUENCE: 5 atg atg tgg acc tgg gca ctg tgg atg ctc ccc tca ctc tgc aaa ttc     48
Met Met Trp Thr Trp Ala Leu Trp Met Leu Pro Ser Leu Cys Lys Phe
```

-continued

| | 1 | | | 5 | | | | 10 | | | | 15 | | | |
|---|---|---|---|---|---|---|---|---|---|---|---|---|---|---|---|
| agc | ctg | gca | gct | ctg | cca | gct | aag | cct | gag | aac | att | tcc | tgt | gtc | tac | 96 |
| Ser | Leu | Ala | Ala | Leu | Pro | Ala | Lys | Pro | Glu | Asn | Ile | Ser | Cys | Val | Tyr | |
| | | | 20 | | | | 25 | | | | | 30 | | | | |

```
agc ctg gca gct ctg cca gct aag cct gag aac att tcc tgt gtc tac      96
Ser Leu Ala Ala Leu Pro Ala Lys Pro Glu Asn Ile Ser Cys Val Tyr
             20              25                  30 tac tat agg aaa aat tta acc tgc act tgg agt cca gga aag gaa acc     144
Tyr Tyr Arg Lys Asn Leu Thr Cys Thr Trp Ser Pro Gly Lys Glu Thr
         35                  40              45 agt tat acc cag tac aca gtt aag aga act tac gct ttt gga gaa aaa     192
Ser Tyr Thr Gln Tyr Thr Val Lys Arg Thr Tyr Ala Phe Gly Glu Lys
     50                  55                  60 cat gat aat tgt aca acc aat agt tct aca agt gaa aat cgt gct tcg     240
His Asp Asn Cys Thr Thr Asn Ser Ser Thr Ser Glu Asn Arg Ala Ser
 65                  70                  75                  80 tgc tct ttt ttc ctt cca aga ata acg atc cca gat aat tat acc att     288
Cys Ser Phe Phe Leu Pro Arg Ile Thr Ile Pro Asp Asn Tyr Thr Ile
                 85                  90                  95 gag gtg gaa gct gaa aat gga gat ggt gta att aaa tct cat atg aca     336
Glu Val Glu Ala Glu Asn Gly Asp Gly Val Ile Lys Ser His Met Thr
             100                 105                 110 tac tgg aga tta gag aac ata gcg aaa act gaa cca cct aag att ttc     384
Tyr Trp Arg Leu Glu Asn Ile Ala Lys Thr Glu Pro Pro Lys Ile Phe
         115                 120                 125 cgt gtg aaa cca gtt ttg ggc atc aaa cga atg att caa att gaa tgg     432
Arg Val Lys Pro Val Leu Gly Ile Lys Arg Met Ile Gln Ile Glu Trp
 130                 135                 140 ata aag cct gag ttg gcg cct gtt tca tct gat tta aaa tac aca ctt     480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct     528
Arg Phe Arg Thr Val Asn Ser Thr Ser Trp Met Glu Val Asn Phe Ala
                 165                 170                 175 aag aac cgt aag gat aaa aac caa acg tac aac ctc acg ggg ctg cag     576
Lys Asn Arg Lys Asp Lys Asn Gln Thr Tyr Asn Leu Thr Gly Leu Gln
             180                 185                 190 cct ttt aca gaa tat gtc ata gct ctg cga tgt gcg gtc aag gag tca     624
Pro Phe Thr Glu Tyr Val Ile Ala Leu Arg Cys Ala Val Lys Glu Ser
         195                 200                 205 aag ttc tgg agt gac tgg agc caa gaa aaa atg gga atg act gag gaa     672
Lys Phe Trp Ser Asp Trp Ser Gln Glu Lys Met Gly Met Thr Glu Glu
 210                 215                 220 gaa gct cca tgt ggc ctg gaa ctg tgg aga gtc ctg aaa cca gct gag     720
Glu Ala Pro Cys Gly Leu Glu Leu Trp Arg Val Leu Lys Pro Ala Glu
225                 230                 235                 240 gcg gat gga aga agg cca gtg cgg ttg tta tgg aag aag gca aga gga     768
Ala Asp Gly Arg Arg Pro Val Arg Leu Leu Trp Lys Lys Ala Arg Gly
                 245                 250                 255 gcc cca gtc cta gag aaa aca ctt ggc tac aac ata tgg tac tat cca     816
Ala Pro Val Leu Glu Lys Thr Leu Gly Tyr Asn Ile Trp Tyr Tyr Pro
             260                 265                 270 gaa agc aac act aac ctc aca gaa aca atg aac act act aac cag cag     864
Glu Ser Asn Thr Asn Leu Thr Glu Thr Met Asn Thr Thr Asn Gln Gln
         275                 280                 285 ctt gaa ctg cat ctg gga ggc gag agc ttt tgg gtg tct atg att tct     912
Leu Glu Leu His Leu Gly Gly Glu Ser Phe Trp Val Ser Met Ile Ser
 290                 295                 300 tat aat tct ctt ggg aag tct cca gtg gcc acc ctg agg att cca gct     960
Tyr Asn Ser Leu Gly Lys Ser Pro Val Ala Thr Leu Arg Ile Pro Ala
305                 310                 315                 320 att caa gaa aaa tca ttt cag tgc att gag gtc atg cag gcc tgc gtt    1008
```

```
Ile Gln Glu Lys Ser Phe Gln Cys Ile Glu Val Met Gln Ala Cys Val
            325                 330                 335 gct gag gac cag cta gtg gtg aag tgg caa agc tct gct cta gac gtg   1056
Ala Glu Asp Gln Leu Val Val Lys Trp Gln Ser Ser Ala Leu Asp Val
        340                 345                 350 aac act tgg atg att gaa tgg ttt ccg gat gtg gac tca gag ccc acc   1104
Asn Thr Trp Met Ile Glu Trp Phe Pro Asp Val Asp Ser Glu Pro Thr
            355                 360                 365 acc ctt tcc tgg gaa tct gtg tct cag gcc acg aac tgg acg atc cag   1152
Thr Leu Ser Trp Glu Ser Val Ser Gln Ala Thr Asn Trp Thr Ile Gln
    370                 375                 380 caa gat aaa tta aaa cct ttc tgg tgc tat aac atc tct gtg tat cca   1200
Gln Asp Lys Leu Lys Pro Phe Trp Cys Tyr Asn Ile Ser Val Tyr Pro
385                 390                 395                 400 atg ttg cat gac aaa gtt ggc gag cca tat tcc atc cag gct tat gcc   1248
Met Leu His Asp Lys Val Gly Glu Pro Tyr Ser Ile Gln Ala Tyr Ala
                405                 410                 415 aaa gaa ggc gtt cca tca gaa ggt cct gag acc aag gtg gag aac att   1296
Lys Glu Gly Val Pro Ser Glu Gly Pro Glu Thr Lys Val Glu Asn Ile
            420                 425                 430 ggc gtg aag acg gtc acg atc aca tgg aaa gag att ccc aag agt gag   1344
Gly Val Lys Thr Val Thr Ile Thr Trp Lys Glu Ile Pro Lys Ser Glu
        435                 440                 445 aga aag ggt atc atc tgc aac tac acc atc ttt tac caa gct gaa ggt   1392
Arg Lys Gly Ile Ile Cys Asn Tyr Thr Ile Phe Tyr Gln Ala Glu Gly
    450                 455                 460 gga aaa gga ttc tcc aag aca gtc aat tcc agc atc ttg cag tac ggc   1440
Gly Lys Gly Phe Ser Lys Thr Val Asn Ser Ser Ile Leu Gln Tyr Gly
465                 470                 475                 480 ctg gag tcc ctg aaa cga aag acc tct tac att gtt cag gtc atg gcc   1488
Leu Glu Ser Leu Lys Arg Lys Thr Ser Tyr Ile Val Gln Val Met Ala
                485                 490                 495 agc acc agt gct ggg gga acc aac ggg acc agc ata aat ttc aag aca   1536
Ser Thr Ser Ala Gly Gly Thr Asn Gly Thr Ser Ile Asn Phe Lys Thr
            500                 505                 510 ttg tca ttc agt gtc ttt gag                                        1557
Leu Ser Phe Ser Val Phe Glu
        515

<210> SEQ ID NO 6
<211> LENGTH: 519
<212> TYPE: PRT
<213> ORGANISM: Homo sapiens

<400> SEQUENCE: 6

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110
```

```
Tyr Trp Arg Leu Glu Asn Ile Ala Lys Thr Glu Pro Lys Ile Phe
            115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
            195                 200                 205

Lys Phe Trp Ser Asp Trp Ser Gln Glu Lys Met Gly Met Thr Glu Glu
            210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
            275                 280                 285

Leu Glu Leu His Leu Gly Gly Glu Ser Phe Trp Val Ser Met Ile Ser
            290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
            355                 360                 365

Thr Leu Ser Trp Glu Ser Val Ser Gln Ala Thr Asn Trp Thr Ile Gln
370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
            435                 440                 445

Arg Lys Gly Ile Ile Cys Asn Tyr Thr Ile Phe Tyr Gln Ala Glu Gly
            450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu
            515
```

```
<210> SEQ ID NO 7
<211> LENGTH: 2748
<212> TYPE: DNA
<213> ORGANISM: Mus musculus
<220> FEATURE:
<221> NAME/KEY: CDS
<222> LOCATION: (237)...(2222)

<400> SEQUENCE: 7 gatgggccc tgaatgttga tctgacagaa ttccagacca acctggtggt tattgtcctt      60
ttcatctggt catgctgaat atactctcaa gatgtgctgg agaaggtgct gctgtccggg     120
ctctcagaga aggcagtgct ggaggcgttc ctggcccggg tctcctccta ctgttcctgg     180
tagcccagcc ttctcggggt ggaaggagaa gctggccagg tgagctctga ggaagc atg     239
                                                                Met
                                                                  1 ctg agc agc cag aag gga tcc tgc agc cag gaa cca ggg gca gcc cac       287
Leu Ser Ser Gln Lys Gly Ser Cys Ser Gln Glu Pro Gly Ala Ala His
          5                  10                  15 gtc cag cct ctg ggt gtg aac gct gga ata atg tgg acc ttg gca ctg       335
Val Gln Pro Leu Gly Val Asn Ala Gly Ile Met Trp Thr Leu Ala Leu
     20                  25                  30 tgg gca ttc tct ttc ctc tgc aaa ttc agc ctg gca gtc ctg ccg act       383
Trp Ala Phe Ser Phe Leu Cys Lys Phe Ser Leu Ala Val Leu Pro Thr
 35                  40                  45 aag cca gag aac att tcc tgc gtc ttt tac ttc gac aga aat ctg act       431
Lys Pro Glu Asn Ile Ser Cys Val Phe Tyr Phe Asp Arg Asn Leu Thr
 50                  55                  60                  65 tgc act tgg aga cca gag aag gaa acc aat gat acc agc tac att gtg       479
Cys Thr Trp Arg Pro Glu Lys Glu Thr Asn Asp Thr Ser Tyr Ile Val
              70                  75                  80 act ttg act tac tcc tat gga aaa agc aat tat agt gac aat gct aca       527
Thr Leu Thr Tyr Ser Tyr Gly Lys Ser Asn Tyr Ser Asp Asn Ala Thr
         85                  90                  95 gag gct tca tat tct ttt ccc cgt tcc tgt gca atg ccc cca gac atc       575
Glu Ala Ser Tyr Ser Phe Pro Arg Ser Cys Ala Met Pro Pro Asp Ile
    100                 105                 110 tgc agt gtt gaa gta caa gct caa aat gga gat ggt aaa gtt aaa tct       623
Cys Ser Val Glu Val Gln Ala Gln Asn Gly Asp Gly Lys Val Lys Ser
115                 120                 125 gac atc aca tat tgg cat tta atc tcc ata gca aaa acc gaa cca cct       671
Asp Ile Thr Tyr Trp His Leu Ile Ser Ile Ala Lys Thr Glu Pro Pro
130                 135                 140                 145 ata att tta agt gtg aat cca att tgt aat aga atg ttc cag ata caa       719
Ile Ile Leu Ser Val Asn Pro Ile Cys Asn Arg Met Phe Gln Ile Gln
                150                 155                 160 tgg aaa ccg cgt gaa aag act cgt ggg ttt cct tta gta tgc atg ctt       767
Trp Lys Pro Arg Glu Lys Thr Arg Gly Phe Pro Leu Val Cys Met Leu
            165                 170                 175 cgg ttc aga act gtc aac agt agc cgc tgg acg gaa gtc aat ttt gaa       815
Arg Phe Arg Thr Val Asn Ser Ser Arg Trp Thr Glu Val Asn Phe Glu
        180                 185                 190 aac tgt aaa cag gtc tgc aac ctc aca gga ctt cag gct ttc aca gaa       863
Asn Cys Lys Gln Val Cys Asn Leu Thr Gly Leu Gln Ala Phe Thr Glu
    195                 200                 205 tat gtc ctg gct cta cga ttc agg ttc aat gac tca aga tat tgg agc       911
Tyr Val Leu Ala Leu Arg Phe Arg Phe Asn Asp Ser Arg Tyr Trp Ser
210                 215                 220                 225 aag tgg agc aaa gaa gaa acc aga gtg act atg gag gaa gtt cca cat       959
Lys Trp Ser Lys Glu Glu Thr Arg Val Thr Met Glu Glu Val Pro His
```

-continued

```
                    230                     235                     240
gtc ctg gac ctg tgg aga att ctg gaa cca gca gac atg aac gga gac    1007
Val Leu Asp Leu Trp Arg Ile Leu Glu Pro Ala Asp Met Asn Gly Asp
                    245                     250                     255 agg aag gtg cga ttg ctg tgg aag aag gca aga gga gcc ccc gtc ttg    1055
Arg Lys Val Arg Leu Leu Trp Lys Lys Ala Arg Gly Ala Pro Val Leu
                    260                     265                     270 gag aaa aca ttt ggc tac cac ata cag tac ttt gca gag aac agc act    1103
Glu Lys Thr Phe Gly Tyr His Ile Gln Tyr Phe Ala Glu Asn Ser Thr
        275                     280                     285 aac ctc aca gag ata aac aac atc acc acc cag cag tat gaa ctg ctt    1151
Asn Leu Thr Glu Ile Asn Asn Ile Thr Thr Gln Gln Tyr Glu Leu Leu
290                     295                     300                     305 ctg atg agc cag gca cac tct gtg tcc gtg act tct ttt aat tct ctt    1199
Leu Met Ser Gln Ala His Ser Val Ser Val Thr Ser Phe Asn Ser Leu
                    310                     315                     320 ggc aag tcc caa gag acc atc ctg agg atc cca gat gtc cat gag aag    1247
Gly Lys Ser Gln Glu Thr Ile Leu Arg Ile Pro Asp Val His Glu Lys
                    325                     330                     335 acc ttc cag tac att aag agc atg cag gcc tac ata gcc gag ccc ctg    1295
Thr Phe Gln Tyr Ile Lys Ser Met Gln Ala Tyr Ile Ala Glu Pro Leu
        340                     345                     350 ttg gtg gtg aac tgg caa agc tcc att cct gcg gtg gac act tgg ata    1343
Leu Val Val Asn Trp Gln Ser Ser Ile Pro Ala Val Asp Thr Trp Ile
        355                     360                     365 gtg gag tgg ctc cca gaa gct gcc atg tcg aag ttc cct gcc ctt tcc    1391
Val Glu Trp Leu Pro Glu Ala Ala Met Ser Lys Phe Pro Ala Leu Ser
370                     375                     380                     385 tgg gaa tct gtg tct cag gtc acg aac tgg acc atc gag caa gat aaa    1439
Trp Glu Ser Val Ser Gln Val Thr Asn Trp Thr Ile Glu Gln Asp Lys
                    390                     395                     400 cta aaa cct ttc aca tgc tat aat ata tca gtg tat cca gtg ttg gga    1487
Leu Lys Pro Phe Thr Cys Tyr Asn Ile Ser Val Tyr Pro Val Leu Gly
                    405                     410                     415 cac cga gtt gga gag ccg tat tca atc caa gct tat gcc aaa gaa gga    1535
His Arg Val Gly Glu Pro Tyr Ser Ile Gln Ala Tyr Ala Lys Glu Gly
                    420                     425                     430 act cca tta aaa ggt cct gag acc agg gtg gag aac atc ggt ctg agg    1583
Thr Pro Leu Lys Gly Pro Glu Thr Arg Val Glu Asn Ile Gly Leu Arg
        435                     440                     445 aca gcc acg atc aca tgg aag gag att cct aag agt gct agg aat gga    1631
Thr Ala Thr Ile Thr Trp Lys Glu Ile Pro Lys Ser Ala Arg Asn Gly
450                     455                     460                     465 ttt atc aac aat tac act gta ttt tac caa gct gaa ggt gga aaa gaa    1679
Phe Ile Asn Asn Tyr Thr Val Phe Tyr Gln Ala Glu Gly Gly Lys Glu
                    470                     475                     480 ctc tcc aag act gtt aac tct cat gcc ctg cag tgt gac ctg gag tct    1727
Leu Ser Lys Thr Val Asn Ser His Ala Leu Gln Cys Asp Leu Glu Ser
        485                     490                     495 ctg aca cga agg acc tct tat act gtt tgg gtc atg gcc agc acc aga    1775
Leu Thr Arg Arg Thr Ser Tyr Thr Val Trp Val Met Ala Ser Thr Arg
        500                     505                     510 gct gga ggt acc aac ggg gtg aga ata aac ttc aag aca ttg tca atc    1823
Ala Gly Gly Thr Asn Gly Val Arg Ile Asn Phe Lys Thr Leu Ser Ile
        515                     520                     525 agt gtg ttt gaa att gtc ctt cta aca tct cta gtt gga gga ggc ctt    1871
Ser Val Phe Glu Ile Val Leu Leu Thr Ser Leu Val Gly Gly Gly Leu
530                     535                     540                     545 ctt cta ctt agc atc aaa aca gtg act ttt ggc ctc aga aag cca aac    1919
```

```
Leu Leu Leu Ser Ile Lys Thr Val Thr Phe Gly Leu Arg Lys Pro Asn
            550                 555                 560 cgg ttg act ccc ctg tgt tgt cct gat gtt ccc aac cct gct gaa agt        1967
Arg Leu Thr Pro Leu Cys Cys Pro Asp Val Pro Asn Pro Ala Glu Ser
            565                 570                 575 agt tta gcc aca tgg ctc gga gat ggt ttc aag aag tca aat atg aag        2015
Ser Leu Ala Thr Trp Leu Gly Asp Gly Phe Lys Lys Ser Asn Met Lys
            580                 585                 590 gag act gga aac tct ggg aac aca gaa gac gtg gtc cta aaa cca tgt        2063
Glu Thr Gly Asn Ser Gly Asn Thr Glu Asp Val Val Leu Lys Pro Cys
            595                 600                 605 ccc gtc ccc gcg gat ctc att gac aag ctg gta gtg aac ttt gag aat        2111
Pro Val Pro Ala Asp Leu Ile Asp Lys Leu Val Val Asn Phe Glu Asn
610                 615                 620                 625 ttt ctg gaa gta gtt ttg aca gag gaa gct gga aag ggt cag gcg agc        2159
Phe Leu Glu Val Val Leu Thr Glu Glu Ala Gly Lys Gly Gln Ala Ser
                630                 635                 640 att ttg gga gga gaa gcg aat gag tat atc tta tcc cag gaa cca agc        2207
Ile Leu Gly Gly Glu Ala Asn Glu Tyr Ile Leu Ser Gln Glu Pro Ser
                645                 650                 655 tgt cct ggc cat tgc tgaagctacc ctcagggtcc aggacagctg tcttgttggc        2262
Cys Pro Gly His Cys
            660 acttgactct ggcaggaacc tgatctctac ttttcttctc cctgtctccg gacactttct       2322 ctccttcatg cagagaccag gactagagcg gattcctcat ggtttgccag gctcctcagt       2382 ccttgctcgg gctcaggatc ttcaacaatg cccttctctgg gacactccat catccactta      2442 tatttatttt ttgcaacatt gtggattgaa cccagggact tgtttatgcg cgcaacttca       2502 gtaactgtgg cagagactta ggaatggaga tctgacccct tgcagaaggt ttctggacat       2562 ccgtccctgt gtgagcctca gacagcattg tctttacttt gaatcagctt ccaagttaat       2622 aaaagaaaaa cagagaggtg gcataacagc tcctgcttcc tgacctgctt gagttccagt       2682 tctgacttcc tttggtgatg aacagcaatg tgggaagtgt aagctgaata aacccttttcc      2742 tcccca                                                                  2748

<210> SEQ ID NO 8
<211> LENGTH: 662
<212> TYPE: PRT
<213> ORGANISM: Mus musculus

<400> SEQUENCE: 8

Met Leu Ser Ser Gln Lys Gly Ser Cys Ser Gln Glu Pro Gly Ala Ala
1               5                   10                  15

His Val Gln Pro Leu Gly Val Asn Ala Gly Ile Met Trp Thr Leu Ala
                20                  25                  30

Leu Trp Ala Phe Ser Phe Leu Cys Lys Phe Ser Leu Ala Val Leu Pro
            35                  40                  45

Thr Lys Pro Glu Asn Ile Ser Cys Val Phe Tyr Phe Asp Arg Asn Leu
        50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
```

```
                115                 120                 125
Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Val Phe Glu Ile Val Leu Leu Thr Ser Leu Val Gly Gly Gly
    530                 535                 540
```

```
Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
            565                 570                 575

Ser Ser Leu Ala Thr Trp Leu Gly Asp Gly Phe Lys Lys Ser Asn Met
        580                 585                 590

Lys Glu Thr Gly Asn Ser Gly Asn Thr Glu Asp Val Val Leu Lys Pro
            595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660
```

<210> SEQ ID NO 9
<211> LENGTH: 2964
<212> TYPE: DNA
<213> ORGANISM: Homo sapiens
<220> FEATURE:
<221> NAME/KEY: CDS
<222> LOCATION: (13)...(2949)

<400> SEQUENCE: 9

```
gaattcgcca cc atg gct cta ttt gca gtc ttt cag aca aca ttc ttc tta      51
              Met Ala Leu Phe Ala Val Phe Gln Thr Thr Phe Phe Leu
                1               5                   10 aca ttg ctg tcc ttg agg act tac cag agt gaa gtc ttg gct gaa cgt        99
Thr Leu Leu Ser Leu Arg Thr Tyr Gln Ser Glu Val Leu Ala Glu Arg
 15              20                  25 tta cca ttg act cct gta tca ctt aaa gtt tcc acc aat tct acg cgt       147
Leu Pro Leu Thr Pro Val Ser Leu Lys Val Ser Thr Asn Ser Thr Arg
30              35                  40                  45 cag agt ttg cac tta caa tgg act gtc cac aac ctt cct tat cat cag       195
Gln Ser Leu His Leu Gln Trp Thr Val His Asn Leu Pro Tyr His Gln
             50                  55                  60 gaa ttg aaa atg gta ttt cag atc cag atc agt agg att gaa aca tcc       243
Glu Leu Lys Met Val Phe Gln Ile Gln Ile Ser Arg Ile Glu Thr Ser
         65                  70                  75 aat gtc atc tgg gtg ggg aat tac agc acc act gtg aag tgg aac cag       291
Asn Val Ile Trp Val Gly Asn Tyr Ser Thr Thr Val Lys Trp Asn Gln
     80                  85                  90 gtt ctg cat tgg agc tgg gaa tct gag ctc cct ttg gaa tgt gcc aca       339
Val Leu His Trp Ser Trp Glu Ser Glu Leu Pro Leu Glu Cys Ala Thr
 95                 100                 105 cac ttt gta aga ata aag agt ttg gtg gac gat gcc aag ttc cct gag       387
His Phe Val Arg Ile Lys Ser Leu Val Asp Asp Ala Lys Phe Pro Glu
110                 115                 120                 125 cca aat ttc tgg agc aac tgg agt tcc tgg gag gaa gtc agt gta caa       435
Pro Asn Phe Trp Ser Asn Trp Ser Ser Trp Glu Glu Val Ser Val Gln
                130                 135                 140 gat tct act gga cag gat ata ttg ttc gtt ttc cct aaa gat aag ctg       483
Asp Ser Thr Gly Gln Asp Ile Leu Phe Val Phe Pro Lys Asp Lys Leu
            145                 150                 155 gtg gaa gaa ggc acc aat gtt acc att tgt tac gtt tct agg aac att       531
Val Glu Glu Gly Thr Asn Val Thr Ile Cys Tyr Val Ser Arg Asn Ile
        160                 165                 170
```

-continued

```
caa aat aat gta tcc tgt tat ttg gaa ggg aaa cag att cat gga gaa      579
Gln Asn Asn Val Ser Cys Tyr Leu Glu Gly Lys Gln Ile His Gly Glu
        175                 180                 185 caa ctt gat cca cat gta act gca ttc aac ttg aat agt gtg cct ttc      627
Gln Leu Asp Pro His Val Thr Ala Phe Asn Leu Asn Ser Val Pro Phe
190                 195                 200                 205 att agg aat aaa ggg aca aat atc tat tgt gag gca agt caa gga aat      675
Ile Arg Asn Lys Gly Thr Asn Ile Tyr Cys Glu Ala Ser Gln Gly Asn
                210                 215                 220 gtc agt gaa ggc atg aaa ggc atc gtt ctt ttt gtc tca aaa gta ctt      723
Val Ser Glu Gly Met Lys Gly Ile Val Leu Phe Val Ser Lys Val Leu
            225                 230                 235 gag gag ccc aag gac ttt tct tgt gaa acc gag gac ttc aag act ttg      771
Glu Glu Pro Lys Asp Phe Ser Cys Glu Thr Glu Asp Phe Lys Thr Leu
        240                 245                 250 cac tgt act tgg gat cct ggg acg gac act gcc ttg ggg tgg tct aaa      819
His Cys Thr Trp Asp Pro Gly Thr Asp Thr Ala Leu Gly Trp Ser Lys
    255                 260                 265 caa cct tcc caa agc tac act tta ttt gaa tca ttt tct ggg gaa aag      867
Gln Pro Ser Gln Ser Tyr Thr Leu Phe Glu Ser Phe Ser Gly Glu Lys
270                 275                 280                 285 aaa ctt tgt aca cac aaa aac tgg tgt aat tgg caa ata act caa gac      915
Lys Leu Cys Thr His Lys Asn Trp Cys Asn Trp Gln Ile Thr Gln Asp
                290                 295                 300 tca caa gaa acc tat aac ttc aca ctc ata gct gaa aat tac tta agg      963
Ser Gln Glu Thr Tyr Asn Phe Thr Leu Ile Ala Glu Asn Tyr Leu Arg
            305                 310                 315 aag aga agt gtc aat atc ctt ttt aac ctg act cat cga gtt tat tta     1011
Lys Arg Ser Val Asn Ile Leu Phe Asn Leu Thr His Arg Val Tyr Leu
        320                 325                 330 atg aat cct ttt agt gtc aac ttt gaa aat gta aat gcc aca aat gcc     1059
Met Asn Pro Phe Ser Val Asn Phe Glu Asn Val Asn Ala Thr Asn Ala
    335                 340                 345 atc atg acc tgg aag gtg cac tcc ata agg aat aat ttc aca tat ttg     1107
Ile Met Thr Trp Lys Val His Ser Ile Arg Asn Asn Phe Thr Tyr Leu
350                 355                 360                 365 tgt cag att gaa ctc cat ggt gaa gga aaa atg atg caa tac aat gtt     1155
Cys Gln Ile Glu Leu His Gly Glu Gly Lys Met Met Gln Tyr Asn Val
                370                 375                 380 tcc atc aag gtg aac ggt gag tac ttc tta agt gaa ctg gaa cct gcc     1203
Ser Ile Lys Val Asn Gly Glu Tyr Phe Leu Ser Glu Leu Glu Pro Ala
            385                 390                 395 aca gag tac atg gcg cga gta cgg tgt gct gat gcc agc cac ttc tgg     1251
Thr Glu Tyr Met Ala Arg Val Arg Cys Ala Asp Ala Ser His Phe Trp
        400                 405                 410 aaa tgg agt gaa tgg agt ggt cag aac ttc acc aca ctt gaa gct gct     1299
Lys Trp Ser Glu Trp Ser Gly Gln Asn Phe Thr Thr Leu Glu Ala Ala
    415                 420                 425 ccc tca gag gcc cct gat gtc tgg aga att gtg agc ttg gag cca gga     1347
Pro Ser Glu Ala Pro Asp Val Trp Arg Ile Val Ser Leu Glu Pro Gly
430                 435                 440                 445 aat cat act gtg acc tta ttc tgg aag cca tta tca aaa ctg cat gcc     1395
Asn His Thr Val Thr Leu Phe Trp Lys Pro Leu Ser Lys Leu His Ala
                450                 455                 460 aat gga aag atc ctg ttc tat aat gta gtt gta gaa aac cta gac aaa     1443
Asn Gly Lys Ile Leu Phe Tyr Asn Val Val Val Glu Asn Leu Asp Lys
            465                 470                 475 cca tcc agt tca gag ctc cat tcc att cca gca cca gcc aac agc aca     1491
Pro Ser Ser Ser Glu Leu His Ser Ile Pro Ala Pro Ala Asn Ser Thr
```

-continued

|  |  |  | 480 |  |  |  |  | 485 |  |  |  |  | 490 |  |  |  |
|---|---|---|---|---|---|---|---|---|---|---|---|---|---|---|---|---|
| aaa | cta | atc | ctt | gac | agg | tgt | tcc | tac | caa | atc | tgc | gtc | ata | gcc | aac | 1539 |
| Lys | Leu | Ile | Leu | Asp | Arg | Cys | Ser | Tyr | Gln | Ile | Cys | Val | Ile | Ala | Asn |  |
| 495 |  |  |  |  |  | 500 |  |  |  |  |  | 505 |  |  |  |  |

| aac | agt | gtg | ggt | gct | tct | cct | gct | tct | gta | ata | gtc | atc | tct | gca | gac | 1587 |
|---|---|---|---|---|---|---|---|---|---|---|---|---|---|---|---|---|
| Asn | Ser | Val | Gly | Ala | Ser | Pro | Ala | Ser | Val | Ile | Val | Ile | Ser | Ala | Asp |  |
| 510 |  |  |  |  | 515 |  |  |  |  | 520 |  |  |  |  | 525 |  |

| ccc | gaa | aac | aaa | gag | gtt | gag | gaa | gaa | aga | att | gca | ggc | aca | gag | ggt | 1635 |
|---|---|---|---|---|---|---|---|---|---|---|---|---|---|---|---|---|
| Pro | Glu | Asn | Lys | Glu | Val | Glu | Glu | Glu | Arg | Ile | Ala | Gly | Thr | Glu | Gly |  |
|  |  |  |  | 530 |  |  |  |  | 535 |  |  |  |  | 540 |  |  |

| gga | ttc | tct | ctg | tct | tgg | aaa | ccc | caa | cct | gga | gat | gtt | ata | ggc | tat | 1683 |
|---|---|---|---|---|---|---|---|---|---|---|---|---|---|---|---|---|
| Gly | Phe | Ser | Leu | Ser | Trp | Lys | Pro | Gln | Pro | Gly | Asp | Val | Ile | Gly | Tyr |  |
|  |  |  |  | 545 |  |  |  |  | 550 |  |  |  |  | 555 |  |  |

| gtt | gtg | gac | tgg | tgt | gac | cat | acc | cag | gat | gtg | ctc | ggt | gat | ttc | cag | 1731 |
|---|---|---|---|---|---|---|---|---|---|---|---|---|---|---|---|---|
| Val | Val | Asp | Trp | Cys | Asp | His | Thr | Gln | Asp | Val | Leu | Gly | Asp | Phe | Gln |  |
|  |  |  | 560 |  |  |  |  | 565 |  |  |  |  | 570 |  |  |  |

| tgg | aag | aat | gta | ggt | ccc | aat | acc | aca | agc | aca | gtc | att | agc | aca | gat | 1779 |
|---|---|---|---|---|---|---|---|---|---|---|---|---|---|---|---|---|
| Trp | Lys | Asn | Val | Gly | Pro | Asn | Thr | Thr | Ser | Thr | Val | Ile | Ser | Thr | Asp |  |
| 575 |  |  |  |  | 580 |  |  |  |  | 585 |  |  |  |  |  |  |

| gct | ttt | agg | cca | gga | gtt | cga | tat | gac | ttc | aga | att | tat | ggg | tta | tct | 1827 |
|---|---|---|---|---|---|---|---|---|---|---|---|---|---|---|---|---|
| Ala | Phe | Arg | Pro | Gly | Val | Arg | Tyr | Asp | Phe | Arg | Ile | Tyr | Gly | Leu | Ser |  |
| 590 |  |  |  |  | 595 |  |  |  |  | 600 |  |  |  |  | 605 |  |

| aca | aaa | agg | att | gct | tgt | tta | tta | gag | aaa | aaa | aca | gga | tac | tct | cag | 1875 |
|---|---|---|---|---|---|---|---|---|---|---|---|---|---|---|---|---|
| Thr | Lys | Arg | Ile | Ala | Cys | Leu | Leu | Glu | Lys | Lys | Thr | Gly | Tyr | Ser | Gln |  |
|  |  |  |  | 610 |  |  |  |  | 615 |  |  |  |  | 620 |  |  |

| gaa | ctt | gct | cct | tca | gac | aac | cct | cac | gtg | ctg | gtg | gat | aca | ttg | aca | 1923 |
|---|---|---|---|---|---|---|---|---|---|---|---|---|---|---|---|---|
| Glu | Leu | Ala | Pro | Ser | Asp | Asn | Pro | His | Val | Leu | Val | Asp | Thr | Leu | Thr |  |
|  |  |  |  | 625 |  |  |  |  | 630 |  |  |  |  | 635 |  |  |

| tcc | cac | tcc | ttc | act | ctg | agt | tgg | aaa | gat | tac | tct | act | gaa | tct | caa | 1971 |
|---|---|---|---|---|---|---|---|---|---|---|---|---|---|---|---|---|
| Ser | His | Ser | Phe | Thr | Leu | Ser | Trp | Lys | Asp | Tyr | Ser | Thr | Glu | Ser | Gln |  |
|  |  |  | 640 |  |  |  |  | 645 |  |  |  |  | 650 |  |  |  |

| cct | ggt | ttt | ata | caa | ggg | tac | cat | gtc | tat | ctg | aaa | tcc | aag | gcg | agg | 2019 |
|---|---|---|---|---|---|---|---|---|---|---|---|---|---|---|---|---|
| Pro | Gly | Phe | Ile | Gln | Gly | Tyr | His | Val | Tyr | Leu | Lys | Ser | Lys | Ala | Arg |  |
|  | 655 |  |  |  |  | 660 |  |  |  |  | 665 |  |  |  |  |  |

| cag | tgc | cac | cca | cga | ttt | gaa | aag | gca | gtt | ctt | tca | gat | ggt | tca | gaa | 2067 |
|---|---|---|---|---|---|---|---|---|---|---|---|---|---|---|---|---|
| Gln | Cys | His | Pro | Arg | Phe | Glu | Lys | Ala | Val | Leu | Ser | Asp | Gly | Ser | Glu |  |
| 670 |  |  |  |  | 675 |  |  |  |  | 680 |  |  |  |  | 685 |  |

| tgt | tgc | aaa | tac | aaa | att | gac | aac | ccg | gaa | gaa | aag | gca | ttg | att | gtg | 2115 |
|---|---|---|---|---|---|---|---|---|---|---|---|---|---|---|---|---|
| Cys | Cys | Lys | Tyr | Lys | Ile | Asp | Asn | Pro | Glu | Glu | Lys | Ala | Leu | Ile | Val |  |
|  |  |  |  | 690 |  |  |  |  | 695 |  |  |  |  | 700 |  |  |

| gac | aac | cta | aag | cca | gaa | tcc | ttc | tat | gag | ttt | ttc | atc | act | cca | ttc | 2163 |
|---|---|---|---|---|---|---|---|---|---|---|---|---|---|---|---|---|
| Asp | Asn | Leu | Lys | Pro | Glu | Ser | Phe | Tyr | Glu | Phe | Phe | Ile | Thr | Pro | Phe |  |
|  |  |  | 705 |  |  |  |  | 710 |  |  |  |  | 715 |  |  |  |

| act | agt | gct | ggt | gaa | ggc | ccc | agt | gct | acg | ttc | acg | aag | gtc | acg | act | 2211 |
|---|---|---|---|---|---|---|---|---|---|---|---|---|---|---|---|---|
| Thr | Ser | Ala | Gly | Glu | Gly | Pro | Ser | Ala | Thr | Phe | Thr | Lys | Val | Thr | Thr |  |
|  | 720 |  |  |  |  | 725 |  |  |  |  | 730 |  |  |  |  |  |

| ccg | gat | gaa | cac | tcc | tcg | atg | ctg | att | cat | atc | cta | ctg | ccc | atg | gtt | 2259 |
|---|---|---|---|---|---|---|---|---|---|---|---|---|---|---|---|---|
| Pro | Asp | Glu | His | Ser | Ser | Met | Leu | Ile | His | Ile | Leu | Leu | Pro | Met | Val |  |
| 735 |  |  |  |  | 740 |  |  |  |  | 745 |  |  |  |  |  |  |

| ttc | tgc | gtc | ttg | ctc | atc | atg | gtc | atg | tgc | tac | ttg | aaa | agt | cag | tgg | 2307 |
|---|---|---|---|---|---|---|---|---|---|---|---|---|---|---|---|---|
| Phe | Cys | Val | Leu | Leu | Ile | Met | Val | Met | Cys | Tyr | Leu | Lys | Ser | Gln | Trp |  |
| 750 |  |  |  |  | 755 |  |  |  |  | 760 |  |  |  |  | 765 |  |

| atc | aag | gag | acc | tgt | tat | cct | gac | atc | cct | gac | cct | tac | aag | agc | agc | 2355 |
|---|---|---|---|---|---|---|---|---|---|---|---|---|---|---|---|---|
| Ile | Lys | Glu | Thr | Cys | Tyr | Pro | Asp | Ile | Pro | Asp | Pro | Tyr | Lys | Ser | Ser |  |
|  |  |  |  | 770 |  |  |  |  | 775 |  |  |  |  | 780 |  |  |

-continued

```
atc ctg tca tta ata aaa ttc aag gag aac cct cac cta ata ata atg      2403
Ile Leu Ser Leu Ile Lys Phe Lys Glu Asn Pro His Leu Ile Ile Met
            785                 790                 795 aat gtc agt gac tgt atc cca gat gct att gaa gtt gta agc aag cca      2451
Asn Val Ser Asp Cys Ile Pro Asp Ala Ile Glu Val Val Ser Lys Pro
        800                 805                 810 gaa ggg aca aag ata cag ttc cta ggc act agg aag tca ctc aca gaa      2499
Glu Gly Thr Lys Ile Gln Phe Leu Gly Thr Arg Lys Ser Leu Thr Glu
    815                 820                 825 acc gag ttg act aag cct aac tac ctt tat ctc ctt cca aca gaa aag      2547
Thr Glu Leu Thr Lys Pro Asn Tyr Leu Tyr Leu Leu Pro Thr Glu Lys
830                 835                 840                 845 aat cac tct ggc cct ggc ccc tgc atc tgt ttt gag aac ttg acc tat      2595
Asn His Ser Gly Pro Gly Pro Cys Ile Cys Phe Glu Asn Leu Thr Tyr
                850                 855                 860 aac cag gca gct tct gac tct ggc tct tgt ggc cat gtt cca gta tcc      2643
Asn Gln Ala Ala Ser Asp Ser Gly Ser Cys Gly His Val Pro Val Ser
            865                 870                 875 cca aaa gcc cca agt atg ctg gga cta atg acc tca cct gaa aat gta      2691
Pro Lys Ala Pro Ser Met Leu Gly Leu Met Thr Ser Pro Glu Asn Val
        880                 885                 890 cta aag gca cta gaa aaa aac tac atg aac tcc ctg gga gaa atc cca      2739
Leu Lys Ala Leu Glu Lys Asn Tyr Met Asn Ser Leu Gly Glu Ile Pro
    895                 900                 905 gct gga gaa aca agt ttg aat tat gtg tcc cag ttg gct tca ccc atg      2787
Ala Gly Glu Thr Ser Leu Asn Tyr Val Ser Gln Leu Ala Ser Pro Met
910                 915                 920                 925 ttt gga gac aag gac agt ctc cca aca aac cca gta gag gca cca cac      2835
Phe Gly Asp Lys Asp Ser Leu Pro Thr Asn Pro Val Glu Ala Pro His
                930                 935                 940 tgt tca gag tat aaa atg caa atg gca gtc tcc ctg cgt ctt gcc ttg      2883
Cys Ser Glu Tyr Lys Met Gln Met Ala Val Ser Leu Arg Leu Ala Leu
            945                 950                 955 cct ccc ccg acc gag aat agc agc ctc tcc tca att acc ctt tta gat      2931
Pro Pro Pro Thr Glu Asn Ser Ser Leu Ser Ser Ile Thr Leu Leu Asp
        960                 965                 970 cca ggt gaa cac tac tgc taaccagcac tcgag                             2964
Pro Gly Glu His Tyr Cys
    975
```

<210> SEQ ID NO 10
<211> LENGTH: 979
<212> TYPE: PRT
<213> ORGANISM: Homo sapiens

<400> SEQUENCE: 10

```
Met Ala Leu Phe Ala Val Phe Gln Thr Thr Phe Phe Leu Thr Leu Leu
  1               5                  10                  15

Ser Leu Arg Thr Tyr Gln Ser Glu Val Leu Ala Glu Arg Leu Pro Leu
             20                  25                  30

Thr Pro Val Ser Leu Lys Val Ser Thr Asn Ser Thr Arg Gln Ser Leu
         35                  40                  45

His Leu Gln Trp Thr Val His Asn Leu Pro Tyr His Gln Glu Leu Lys
     50                  55                  60

Met Val Phe Gln Ile Gln Ile Ser Arg Ile Glu Thr Ser Asn Val Ile
 65                  70                  75                  80

Trp Val Gly Asn Tyr Ser Thr Thr Val Lys Trp Asn Gln Val Leu His
                 85                  90                  95

Trp Ser Trp Glu Ser Glu Leu Pro Leu Glu Cys Ala Thr His Phe Val
```

```
                    100                 105                 110
Arg Ile Lys Ser Leu Val Asp Asp Ala Lys Phe Pro Glu Pro Asn Phe
            115                 120                 125

Trp Ser Asn Trp Ser Ser Trp Glu Glu Val Ser Val Gln Asp Ser Thr
130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525
```

```
Lys Glu Val Glu Glu Arg Ile Ala Gly Thr Glu Gly Phe Ser
    530                 535                 540
Leu Ser Trp Lys Pro Gln Pro Gly Asp Val Ile Gly Tyr Val Val Asp
545                 550                 555                 560
Trp Cys Asp His Thr Gln Asp Val Leu Gly Asp Phe Gln Trp Lys Asn
                565                 570                 575
Val Gly Pro Asn Thr Thr Ser Thr Val Ile Ser Thr Asp Ala Phe Arg
                580                 585                 590
Pro Gly Val Arg Tyr Asp Phe Arg Ile Tyr Gly Leu Ser Thr Lys Arg
                595                 600                 605
Ile Ala Cys Leu Leu Glu Lys Lys Thr Gly Tyr Ser Gln Glu Leu Ala
            610                 615                 620
Pro Ser Asp Asn Pro His Val Leu Val Asp Thr Leu Thr Ser His Ser
625                 630                 635                 640
Phe Thr Leu Ser Trp Lys Asp Tyr Ser Thr Glu Ser Gln Pro Gly Phe
                645                 650                 655
Ile Gln Gly Tyr His Val Tyr Leu Lys Ser Lys Ala Arg Gln Cys His
                660                 665                 670
Pro Arg Phe Glu Lys Ala Val Leu Ser Asp Gly Ser Glu Cys Cys Lys
                675                 680                 685
Tyr Lys Ile Asp Asn Pro Glu Glu Lys Ala Leu Ile Val Asp Asn Leu
            690                 695                 700
Lys Pro Glu Ser Phe Tyr Glu Phe Phe Ile Thr Pro Phe Thr Ser Ala
705                 710                 715                 720
Gly Glu Gly Pro Ser Ala Thr Phe Thr Lys Val Thr Thr Pro Asp Glu
                725                 730                 735
His Ser Ser Met Leu Ile His Ile Leu Leu Pro Met Val Phe Cys Val
                740                 745                 750
Leu Leu Ile Met Val Met Cys Tyr Leu Lys Ser Gln Trp Ile Lys Glu
            755                 760                 765
Thr Cys Tyr Pro Asp Ile Pro Asp Pro Tyr Lys Ser Ser Ile Leu Ser
    770                 775                 780
Leu Ile Lys Phe Lys Glu Asn Pro His Leu Ile Ile Met Asn Val Ser
785                 790                 795                 800
Asp Cys Ile Pro Asp Ala Ile Glu Val Val Ser Lys Pro Glu Gly Thr
                805                 810                 815
Lys Ile Gln Phe Leu Gly Thr Arg Lys Ser Leu Thr Glu Thr Glu Leu
                820                 825                 830
Thr Lys Pro Asn Tyr Leu Tyr Leu Leu Pro Thr Glu Lys Asn His Ser
            835                 840                 845
Gly Pro Gly Pro Cys Ile Cys Phe Glu Asn Leu Thr Tyr Asn Gln Ala
    850                 855                 860
Ala Ser Asp Ser Gly Ser Cys Gly His Val Pro Val Ser Pro Lys Ala
865                 870                 875                 880
Pro Ser Met Leu Gly Leu Met Thr Ser Pro Glu Asn Val Leu Lys Ala
                885                 890                 895
Leu Glu Lys Asn Tyr Met Asn Ser Leu Gly Glu Ile Pro Ala Gly Glu
                900                 905                 910
Thr Ser Leu Asn Tyr Val Ser Gln Leu Ala Ser Pro Met Phe Gly Asp
            915                 920                 925
```

-continued

```
Lys Asp Ser Leu Pro Thr Asn Pro Val Glu Ala Pro His Cys Ser Glu
    930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```

METHODS OF PREDICTING THERAPEUTIC RESPONSE IN ATOPIC DERMATITIS TO IL-31 ANTAGONISTS

CROSS-REFERENCE TO RELATED APPLICATIONS

This application is a divisional of U.S. application Ser. No. 11/353,454, filed Feb. 14, 2006, now abandoned which claims the benefit of U.S. Provisional Application Ser. No. 60/653,114, filed Feb. 14, 2005, U.S. Provisional Application Ser. No. 60/716,762, filed Sep. 13, 2005, and U.S. Provisional Application Ser. No. 60/749,952, filed Dec. 13, 2005, all of which are herein incorporated by reference.

BACKGROUND OF THE INVENTION

The skin plays an important role in the immune system and consists of layers. Circulating T lymphocytes migrate to the skin under normal and inflammatory conditions. The cutaneous lymphocyte antigen (CLA) is considered a homing receptor for T cells with tropism for the skin. Santamaria-Babi, L., *Eur. J. Dermatol.* 14:13-18, 2004. CLA is a carbohydrate structure which is expressed on memory T cells as an epitope of the single cell-surface protein named P-selectin glycoprotein ligand-1 (PSGL-1) and facilitates binding of T cells to E-selectin, an inducible adhesion molecule expressed on vascular endothelium. See Fuhlbrigge R C, et al., *Nature* 1997; 389:978-81.

Several diseases of the skin are known to express high levels of CLA+ T cells, including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. There is a need to treat such skin T cell mediated diseases.

The demonstrated in vivo activities of cytokines illustrate the enormous clinical potential of, and need for, other cytokines, cytokine agonists, and cytokine antagonists. The present invention addresses these needs by providing a method of treating such diseases by interfering with the actions of IL-31, a newly identified cytokine. IL-31, when over-expressed in mice, results initching and dermatitis-like symptoms. Both skin-homing T cells and epidermal keratinocytes have been implicated in the pathology of skin diseases in humans.

The present invention provides such polypeptides for these and other uses that should be apparent to those skilled in the art from the teachings herein.

SUMMARY OF THE INVENTION

Within one aspect, the invention provides a method of treating atopic dermatitis diseased skin comprising administering an antagonist molecule to a mammal with the diseased skin wherein the diseased skin is characterized by cutaneous lymphocyte antigen positive T cells and the antagonist molecule specifically binds to the polypeptide comprising the amino acid sequence as shown in SEQ ID NO:2 or SEQ ID NO: 4, and whereby administration of the antagonist molecule improves, prevents, inhibits or reduces the diseased skin. Within another embodiment, the antagonist is an antibody or antibody fragment. Within a further embodiment the antagonist molecule specifically binds to the polypeptide comprising the amino acid sequence as shown in SEQ ID NO:2. Within another embodiment, the atopic dermatitis diseased skin is pruritic.

Within another aspect, the invention provides a method for treating pruritis from atopic dermatitis comprising administering an antagonist molecule to a mammal with the pruritis wherein the pruritis is characterized by cutaneous lymphocyte antigen positive T cells and wherein the antagonist molecule specifically binds to the polypeptide having the amino acid sequence as shown in SEQ ID NO:2 or in SEQ ID NO: 4, and whereby administration of the antagonist molecule improves, prevents, inhibits or reduces the pruritis. Within an further embodiment, the mammal is a human. Within a further embodiment, the antagonist is an antibody or antibody fragment. Within a further embodiment, the antagonist molecule specifically binds to the polypeptide comprising the amino acid sequence as shown in SEQ ID NO:2.

Within another aspect, the invention provides a method for predicting therapeutic response to an IL-31 antagonist in an individual with atopic dermatitis in need of IL-31 antagonist therapy comprising obtaining a biological sample from the patient, isolating circulating cutaneous lymphocyte positive T cells from the biological sample, and detecting IL-31 production from the isolated cutaneous lymphocyte positive T cells. Within an embodiment, the IL-31 is detected by specifically binding to an IL-31 antagonist. Within a further embodiment, the IL-31 antagonist is an anti-IL-31 antibody or antibody fragment. Within another embodiment, the antagonist molecule specifically binds to the polypeptide comprising the amino acid sequence as shown in SEQ ID NO:2. Within another embodiment, the method comprises the additional step of stimulating or activating the cutaneous lymphocyte antigen positive T cells. Within a further embodiment, the IL-31 is detected by specifically binding to an IL-31 antagonist. Within another embodiment, the IL-31 antagonist molecule is an anti-IL-31 antibody or antibody fragment. Within a further embodiment, the antagonist molecule specifically binds to the polypeptide comprising the amino acid sequence as shown in SEQ ID NO:2.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e., invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides novel methods of using IL-31 polynucleotides, polypeptides, and antagonists in detection, diagnosis, and treatment of diseases, in particular, diseases that are mediated by cutaneous lymphocyte antigen (CLA) positive T cells. The present invention is based in part upon the discovery that a previously identified cytokine, IL-31 is expressed by skin-homing T cells, but not gut-homing T cells.

IL-31 is a recently discovered protein having the structure of a four-helical-bundle cytokine. This cytokine was previously identified as IL-31 and is fully described in U.S. patent application Ser. No. 10/352,554, filed Jan. 21, 2003. See published U.S. Patent Application No. 2003-0224487, and PCT application WO 03/060090, all herein incorporated by reference. See also, Dillon, et al., *Nature Immunol.* 5:752-760, 2004. IL-31 is a ligand with high specificity for the receptor IL-31RA and at least one additional subunit comprising OncostatinM receptor beta (OSMRbeta). The native polynucleotide and polypeptide sequences for human IL-31 are shown in SEQ ID NOs: 1 and 2, respectively. The native polynucleotide and polypeptide sequences for mouse IL-31 are shown in SEQ ID NOs: 3 and 4, respectively. The native polynucleotide and polypeptide sequences for human IL-31RA are shown in SEQ ID NOs: 5 and 6, respectively. The native polynucleotide and polypeptide sequences for mouse IL-31RA are shown in SEQ ID NOs: 7 and 8, respectively. The native polynucleotide and polypeptide sequences for human OSMRbeta are shown in SEQ ID NOs: 9 and 10, respectively.

The secretory signal sequence of IL-31 is comprised of amino acid residues 1 (Met) to 23 (Ala), and the mature polypeptide is comprised of amino acid residues 24 (Ser) to 164 (Thr) as shown in SEQ ID NO:2. Further N-terminal sequencing analysis of purified IL-31 from 293T cells showed an N-terminus at residue 27 (Leu) as shown in SEQ ID NO:2, with the mature polypeptide comprised of amino acid residues 27 (Leu) to 164 (Thr) as shown in SEQ ID NO:2.

As used herein the term, IL-31 means Zcytor17lig, and IL-31RA means Zcytor17, as used in U.S. patent publication number 20030224487 (herein incorporated by reference), as shown above. The heterodimeric receptor for IL-31 was also described in 2003-0096339 (also incorporated herein by reference) as zcytor17 (HUGO name, IL-31RA) which form a heterodimer with at least one additional subunit comprising OncostatinM receptor beta (OSMRbeta).

Both skin-homing T cells and epidermal kerationcytes have been implicated in the pathology of skin diseases in humans. As shown herein, IL-31 mRNA and protein expression is restricted to the skin-homing CLA+ T cell population in both atopic dermatitis (AD) patients and normal individuals, while analysis of the receptor for IL-31, IL-31RA, by immunohistochemistry (IHC) suggests slightly higher levels of IL-31RA expression on skin keratinocytes in skin biopsies from AD sufferers compared to normal individuals.

When over-expressed in mice, IL-31 results in pruritus and the development of skin dermatitis resembling human atopic dermatitis (AD). Immunohistochemistry (IHC) studies shown herein show that IL-31RA protein was expressed by skin keratinocytes and infiltrating macrophages in skin biopsies from AD patients. Comparisons between AD patients and normal individuals suggested that IL-31RA was expressed at higher levels on epidermal keratinocytes in the AD samples. Skin cell infiltrates, which were present at greater numbers in skin of AD patients compared to normal individuals, expressed IL-31 mRNA. Histomorphometric analysis of these cells suggested a lymphocytic lineage with the majority of cells staining positive for cutaneous lymphocyte antigen (CLA) and CD3, demonstrating that skin-homing T cells in skin express IL-31 mRNA. Upon analysis of peripheral blood T cells for IL-31, IL-31 mRNA and protein expression is largely restricted to CD45RO+ CLA+ skin-homing T cells in AD and normal volunteers. Moreover, circulating CLA+ T cells from AD patients are capable of producing higher levels of IL-31 compared to CLA+ T cells from normal individuals, though there is large variability between patient samples. These results provide strong evidence that IL-31 expression may contribute to the development of AD skin inflammation and pruritus.

As shown herein, IL-31 is produced both locally in the skin and by skin infiltrating cells. Local production of cytokines in tissues by T cells is thought to be a key mechanism for disease pathogenesis in AD and increased numbers of T cells both in circulation and in skin is thought to correlate with disease.

Although both AD patients and normal controls have circulating CLA+ T cells that express IL-31 upon activation, CLA+ T cells from AD patients are reported to exist in a more activated state compared to cells from normal individuals. See Akdis M, *J Immunol* 159:4611-4619, 1997. Consequently, the threshold of stimulation required for the production of IL-31 by CLA+ T cells may differ between dermatitis patients and control subjects. As shown herein, circulating CLA+ T cells from AD patients after 24 hours of stimulation with sub-optimal concentrations of anti-CD3 in the absence of anti-CD28 have the capacity to produce higher levels of IL-31 compared to cells from normal individuals. Due to the variability in IL-31 levels produced by CLA+ T cells from individual AD patients, there was no significant difference in the average IL-31 production from circulating CLA+ T cells of AD and normal individuals. Nevertheless, since more CLA+ T cells are localized in skin of AD patients, as compared to normal individuals, there is an increased potential for IL-31 activity in the AD skin micro-environment.

Example 8 demonstrates that circulating CLA+ T cells from some AD patients produce higher levels of IL-31 compared to cells from normal individuals. The detection of IL-31 in patients of such a subpopulation using the bioassay provided herein, or with any assay that detects IL-31 produced by circulating T cells in the blood, may be useful to determine if an IL-31 antagonist will be useful as treatment for diseases wherein the presence of IL-31 causes inflammation.

A cell line that is dependent on the OSMRbeta and IL-31RA linked pathway for survival and growth in the absence of other growth factors can be used to measure the activity of IL-31. Such growth factor-dependent cell lines include BaF3, FDC-P1, and MO7e. For information on the BaF3 cell line, see Palacios and Steinmetz, (*Cell* 41: 727-734, 1985) and Mathey-Prevot et al., (*Mol. Cell. Biol.* 6: 4133-4135, 1986). For information on the FDC-P1 cell line, see Hapel et al. (*Blood* 64: 786-790, 1984). For information on the MO7e cell line, see Kiss et al., (*Leukemia* 7: 235-240, 1993).

The amino acid sequence for the OSMR, and IL-31RA receptors indicated that the encoded receptors belonged to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in *Cytokine* 5(2): 95-106, 1993). The IL-31RA receptor is fully described in PCT Patent Application No. US01/20484 (WIPO publication No. WO 02/00721). Analysis of the tissue distribution of the mRNA of the IL-31RA receptor revealed expression in activated CD4+ and CD8+ T-cell subsets, CD14+ monocytes, and weaker expression in CD19+ B-cells. Moreover, the mRNA was present in both resting or activated monocytic cell lines THP-1 (ATCC No. TIB-202), U937 (ATCC No. CRL-1593.2) and HL60 (ATCC No. CCL-240).

IL-31 is considered a four-alpha helix structure. Referring to the human IL-31 amino acid sequence shown in SEQ ID NO:2, the IL-31 helix A is defined by amino acid residues 38-52; helix B by amino acid residues 83-98; helix C by amino acid residues 104-117; and helix D by amino acid residues 137-152, and the conserved cysteine residues within IL-31 correspond to amino acid residues 72, 133, and 147 of SEQ ID NO:2; and 74, 137, and 151 of SEQ ID NO:8 described herein. Also highly conserved in the IL-31 is the Glu residue as shown in SEQ ID NO:2 at residue 43.

The polynucleotide sequence for the mouse ortholog of IL-31 has been identified and is shown in SEQ ID NO:3 and the corresponding amino acid sequence shown in SEQ ID NO:4. For the IL-31 mouse cytokine amino acid sequence of SEQ ID NO: 4, helix A is defined by amino acid residues 38-52; helix B by amino acid residues 85-98; helix C by amino acid residues 104-118; and helix D by amino acid residues 141-157. Mature sequence for the mouse IL-31 putatively begins at $Met_1$, as shown in SEQ ID NO:4, which corresponds to $Met_1$, as shown in SEQ ID NO:2, in the human sequence. Tissue analysis revealed that expression of mouse IL-31 is found in testis, brain, CD90+ cells, prostate cells, salivary gland and skin. Further N-terminal sequencing analysis of purified IL-31 from 293T cells showed an N-terminus at residue 31 (Ala) as shown in SEQ ID NO:4 with the mature polypeptide comprising amino acid residues 31 (Ala) to 163 (Cys).

IL-31 is located at the 12q24.31 region of chromosome 12. Thus, the present invention also provides reagents which will find use in diagnostic applications. For example, the IL-31 gene, a probe comprising IL-31 DNA or RNA or a subsequence thereof, can be used to determine if the IL-31 gene is present on a human chromosome, such as chromosome 12, or if a gene mutation has occurred. Detectable chromosomal aberrations at the IL-31 gene locus include, but are not limited to, aneuploidy, gene copy number changes, loss of heterozygosity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995). Detection of chromosomal aberrations may be particularly important for diseases with a high correlation of cutaneous lymphocyte antigen. Thus, the present invention includes methods of detecting changes in the IL-31 gene, including up or down regulations thereof.

The proteins of the present invention (or polypeptide fragments thereof) can be joined to other bioactive molecules, particularly other cytokines, to provide multi-functional molecules. For example, one or more helices from IL-31 can be joined to other cytokines to enhance their biological properties or efficiency of production.

The present invention also provides the use of detecting polypeptide fragments or peptides comprising an epitope-bearing portion of a IL-31 polypeptide described herein in diseases mediated by CLA positive T cells. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies (e.g., neutralizing antibodies) that bind with the polypeptides described herein. Hopp/Woods hydrophilicity profiles can be used to determine regions that have the most antigenic potential (Hopp et al., 1981, ibid. and Hopp, 1986, ibid.). For example, in human IL-31, hydrophilic regions include amino acid residues 54-59 of SEQ ID NO:2, amino acid residues 129-134 of SEQ ID NO:2, amino acid residues 53-58 of SEQ ID NO:2, amino acid residues 35-40 of SEQ ID NO:2, and amino acid residues 33-38 of SEQ ID NO:2. For example, in mouse IL-31, hydrophilic regions include amino acid residues 34-39 of SEQ ID NO:4, amino acid residues 46-51 of SEQ ID NO:4, amino acid residues 131-136 of SEQ ID NO:4, amino acid residues 158-163 of SEQ ID NO:4, and amino acid residues 157-162 of SEQ ID NO:4.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:4. Such epitope-bearing peptides and polypeptides can be produced by fragmenting a IL-31 polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology, pages 9.3.1-9.3.5 and pages 9.4.1-9.4.11* (John Wiley & Sons 1997).

The IL-31 polypeptides of the present invention, including full-length polypeptides, functional fragments, and fusion polypeptides, can be produced, purified and refolded by methods well-known in the art and as described in published U.S. Patent Application No. 2003-0224487, and PCT application WO 03/060090. It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

The present invention provides methods for using IL-31 antagonists, including anti-IL-31 antibodies for reducing, inhibiting, or preventing inflammation in cell microenvironments where one or more cells in the microenvironment is/are T cells that are positive for the cutaneous lymphocyte antigen. In addition the present invention provides methods for using IL-31 antagonists, including anti-IL-31 antibodies for reducing, inhibiting, or preventing itching and pruritis in cell microenvironments where one or more cells in the microenvironment is/are T cells that are positive for the cutaneous lymphocyte antigen.

Antibodies from an immune response generated by inoculation of an animal with IL-31 antigens can be isolated and purified are know in the art and are described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication No. WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-IL-31 antibodies herein bind to a IL-31 polypeptide, peptide or epitope with an affinity at least 10-fold greater than the binding affinity to control (non-IL-31) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Antibodies to IL-31 may be used for tagging cells that express IL-31; for isolating IL-31 by affinity purification; for diagnostic assays for determining circulating levels of IL-31 polypeptides; for detecting or quantitating soluble IL-31 as a marker of underlying pathology or disease; in analytical methods employing FACS; for screening expression libraries; for generating anti-idiotypic antibodies; and as neutralizing antibodies or as antagonists to block IL-31 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-31 or fragments thereof may be used in vitro to detect denatured IL-31 or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Binding polypeptides can also act as IL-31 "antagonists" to block IL-31 binding and signal transduction in vitro and in vivo. These anti-IL-31 binding polypeptides would be useful for inhibiting IL-31 activity or protein-binding.

Both skin-homing T cells and epidermal keratinocytes have been implicated in the pathology of skin diseases in humans. As shown in Example 1 herein, of the T cell subsets, IL-31 mRNA and protein expression is restricted to the skin-homing CLA+ T cell population in humans. As such, an antagonist to IL-31, including an antibody or receptor antagonist will be useful in treating skin and epidermal diseases which are mediated by CLA+ T cells. Such diseases include, for example, atopic dermatitis, contact dermatitis, psoriasis, drug-induced allergic reactions, skin-tropic viruses and viral associated pruritus, vitiligo, cutaneous T cell lymphoma, alopecia aerata, acne rosacea, acne vulgaris, prurigo nodularis, and bullous pemphigoid.

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J. M., *Arch Dermatol:* 135, 1551 (1999). Histopathology reveals spongiosis, hyper and focal parakeratosis in acute lesions, whereas marked epidermal hyperplasia with hyper and parakeratosis, acanthosis/hypergranulosis and perivascular infiltration of the dermis with lymphocytes and abundant mast cells are the hallmarks of chronic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol:* 14, 13, (2004)). A significant increase in circulating CLA+ T cells among AD patients compared with control individuals has been documented (See Teraki Y., et al., *Br J Dermatol:* 143, 373 (2000)), while others have demonstrated that memory CLA+ T cells from AD patients preferentially respond to allergen extract compared to the CLA− population (See Santamaria-Babi, L. F., et al., *J Exp Med:* 181, 1935, (1995)). In humans, the pathogenesis of atopic disorders of the skin have been associated with increases in CLA+ T cells that express increased levels of Th-2-type cytokines like IL-5 and IL-13 9, 10. See Akdis M., et al., *Eur J Immunol:* 30, 3533 (2000); and Hamid Q., et al., *J Allergy Clin Immunol:* 98, 225 (1996).

NC/Nga Mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy:* 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101: 1614, (1998). This protocol can be modified in order to induce skin barrier disregulation and pruritis by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model are used to investigate expression of IL-31 and IL-31RA in AD. See Example 3.

An IL-31 neutralizing antagonist could be effective in inhibiting, reducing, minimizing or preventing atopic dermatitis reactions.

Contact Dermatitis

Allergic contact dermatitis is defined as a T cell mediated immune reaction to an antigen that comes into contact with the skin. The CLA+ T cell population is considered to be involved in the initiation of dermatitis since allergen dependent T cell responses are largely confined to the CLA+ population of cells (See Santamaria-Babi, L. F., et al., *J Exp Med:* 181, 1935, (1995)). Recent data has found that only memory (CD45RO+) CD4+ CLA+ and not CD8+ T cells proliferate and produce both type-1 (IFN-γ) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol:* 51, 32, (2004).

In animal models, it has been demonstrated that allergic contact dermatitis is T-cell dependent and that the allergic-responsive T cells migrate to the site of allergen application. See generally: Engeman T. M., et al., *J Immunol:* 164, 5207, (2000); Ferguson T. A. & Kupper T. S. *J Immunol:* 150, 1172, (1993); and Gorbachev A. V. & Fairchild R. L. *Crit. Rev Immunol:* 21, 451 (2001). Since CLA+ T cells produce IL-31 and IL-31 stimulation of skin keratinocytes can induce proinflammatory chemokines, IL-31 may be involved in the pathophysiology of contact dermatitis. See Example 2 for an in vivo model of contact dermatitis.

An IL-31 neutralizing antagonist could be effective in inhibiting, reducing, minimizing or preventing contact dermatitis reactions.

Drug-Induced Delayed Type Cutaneous Allergic Reactions

Drug-induced delayed type cutaneous allergic reactions are very heterogeneous and may mirror many distinct pathophysiological events. See Brockow K., et al., *Allergy:* 57, 45 (2002). Immunological mechanisms involved in these reactions have been shown as either antibody or cell mediated. In immediate drug allergy an IgE-mediated antibody reaction can be demonstrated by a positive skin prick and/or intradermal test after 20 min, whereas non-immediate reactions to drugs can occur more than one hour after last drug intake and are often T-cell mediated. Non-immediate T-cell mediated delayed type reactions can occur in patients with adverse drug reactions to penicillins for example. Proliferative T cell responses to penicillins have been shown to be restricted to the memory (CD45RO+) CLA+ subpopulation of T cells from penicillin allergic patients whereas the CD45RO+ CLA− subset shows no proliferative response. See Blanca M., Leyva L., et al., *Blood Cells Mol Dis:* 31, 75 (2003). Delayed-type hypersensitivity (DTH) reactions can be artificially reproduced in mice, allowing assessment of factors that may be involved in the initiation and perpetuation of the DTH response. An IL-31 neutralizing antagonist could be effective in inhibiting, reducing, minimizing or preventing delayed type hypersensitivity reactions. See Example 4 for an in vivo model of DTH.

Toxic epidermal necrolysis (TEN) is a very rare but extremely severe drug reaction characterized by widespread apoptosis of epidermis with extensive blisters. Studies have shown that lymphocytes infiltrating the blister are CLA+ T cells and can exhibit cytotoxicity towards epidermal keratinocytes. See Leyva L., et al., *J Allergy Clin Immunol:* 105, 157 (2000); and Nassif A., Bensussan A., et al., *J Allergy Clin Immunol:* 114, 1209 2004). A transgenic mouse system, whereby OVA is expressed under the control of the keratin-5 (K5) promoter in the epidermal and hair follicular keratinocytes of mice, has been generated to establish an animal model for TEN. OVA specific CD8+ T cells, when adoptively transferred into K5-OVA mice, undergo activation and proliferation in the skin-draining lymph nodes and target the skin of K5-OVA mice, resulting in development of skin lesions that are reminiscent of TEN. See Azukizawa H., et al., *Eur J Immunol:* 33, 1879 (2003). An IL-31 neutralizing antagonist could be effective in inhibiting, reducing, minimizing or preventing TEN reactions.

Bullous Pemphigoid

Bullous pemphigoid is a subepidermal disorder which manifests as subepidermal blisters with a dermal infiltrate of neutrophils and eosinophils. Diagnosis is characterized by the presence of antigen-specific antibodies against specific adhesion proteins of the epidermis and dermal-epidermal junction. See Jordon R. E., et al., *JAMA:* 200, 751 (1967). Studies analyzing the role of T cells in the pathogenesis of bullous pemphigoid by analysis of PBL and skin blister T cells have found a predominance of CLA+ T cells expressing increased levels of Th2-cytokines like IL-4 and IL-13. See Teraki Y., et al., *J Invest Dermatol:* 117, 1097 (2001). In bullous pemphigoid patients following therapy with systemic corticosteroids, the frequency of CLA+, but not CLA−, interleukin-13-producing cells is significantly decreased. Decreases in CLA+ cells following corticosteroid treatment is associated with clinical improvement. See Teraki, ibid. Neutralization of IL-31 may improve clinical outcome of bullous pemohigoid. An IL-31 neutralizing antagonist could be effective in inhibiting, reducing, minimizing or preventing bullous pemphigoid.

Alopecia Areata

Alopecia areata (AA) is regarded as a tissue-restricted autoimmune disease of hair follicles in which follicular activity is arrested because of the continued activity of lymphocytic infiltrates. AA results in patches of complete hair loss anywhere on the body, though actual loss of hair follicles does not occur, even in hairless lesions. Although clinical signs of inflammation are absent, skin biopsies from sites of active disease show perifollicular lymphocytic inflammation of primarily CD4+ cells, along with a CD8+ intrafollicular infiltrate. See Kalish R. S. & Gilhar A. *J Investig Dermatol Symp Proc:* 8, 164 (2003).

Studies have shown that scalp skin infiltrating CD4+ or CD8+ lymphocytes express CLA and, in peripheral blood of individuals with AA, the percent of CLA+ CD4+ or CD8+ lymphocytes is significantly higher than that of normal controls. Furthermore, patients with severe or progressive AA show a much higher CLA-positively compared to patients recovering from the disease and a decrease in percent CLA+ cells parallels a good clinical course. See Yano S., et al., *Acta Derm Venereol:* 82, 82 (2002). These studies therefore suggest that CLA+ lymphocytes may play an important role in AA. Xenograft models have demonstrated that activated T cells are likely to play a role in the pathogenesis of AA. Lesional scalp from AA patients grafted onto nude mice regrows hair coincident with a loss of infiltrating lymphocytes from the graft and, transfer of activated lesional T cells to SCID mice can transfer hair loss to human scalp explants on SCID mice. See Kalish R. S. & Gilhar A. *J Investig Dermatol Symp Proc:* 8, 164 (2003).

A variety of immunomodulating therapies are part of the usual treatment for this disorder however none of these treatments have been consistent in their efficacy. See Tang L., et al., *J Invest Dermatol:* 120, 400 (2003); Tang L., et al., (2004); and Tang L., et al., *J Am Acad Dermatol:* 49, 1013 (2003). Neutralizing anti-IL-31 antibody may be effective to limit, reduce, inhibit, or prevent the effects of the development of AA.

Acne Vulgaris/Acne Rosacea

Acne vulgaris, a disorder of the pilosebaceous apparatus, is the most common skin problem of adolescence. Abnormalities in follicular keratinization are thought to produce the acne lesion. Acne rosacea is differentiated from acne vulagaris by the presence of red papules, pustules, cysts and extensive telangiectasias, but the absence of comedones (white heads). Increased sebum excretion from sebaceous glands is a major factor in the pathophysiology of acne vulgarism. Other sebaceous gland functions are also associated with the development of acne, including sebaceous proinflammatory lipids; different cytokines produced locally; periglandular peptides and neuropeptides, such as corticotrophin-releasing hormone, which is produced by sebocytes; and substance P, which is expressed in the nerve endings at the vicinity of healthy-looking glands of acne patients. See Zouboulis C. C. *Clin Dermatol:* 22, 360 (2004).

Although the pathophysiology of acne vulgaris and acne rosacea remains unknown, clinical observations and histopathologic studies suggest that inflammation of the pilosebaceous follicle may be central to the pathogenesis of rosacea and acne vulgarism Early studies on analysis of T cell subsets infiltrating rosacea legions indicated that the majority of T cells expressed CD4. See Rufli T. & Buchner S. A. *Dermatologica:* 169, 1 (1984).

CD4+ T cells produce IL-31 and IHC analysis of skin for IL-31 expression suggests that IL-31 is expressed in sebaceous and sweat glands. IL-31 stimulation of epidermal keratinocytes induces expression of chemokines which likely results in cellular infiltration suggesting that IL-31 may contribute to the pro-inflammatory response in skin. IL-31 may therefore contribute to the pathophysiology of acne rosacea and acne vulgarism Neutralization of IL-31 may improve clinical outcome of acne vulgaris and acne rosacea. An IL-31 neutralizing antagonist could be effective in inhibiting, reducing, minimizing or preventing acne vulgaris and acne rosacea.

Prurigo Nodularis

Prurigo nodularis is an eruption of lichenified or excoriated nodules caused by intractable pruritus that is difficult to treat. While chronic rubbing results in lichenification, and scratching in linear excoriations, individuals who pick and gouge at their itchy, irritated skin tend to produce markedly thickened papules known as prurigo nodules. Although prurigo nodularis is not specific to atopic dermatitis, many patients with these nodules also have an atopic reaction, which manifests as allergic rhinitis, asthma, or food allergy. T cells represent the majority of infiltrating cells in prurigo lesions and these lesions often represents the most pruritic skin lesion in atopy patients.

Topical treatment of prurigo nodularis with capsaicin, an anti-pruritic alkaloid that interferes with the perception of pruritis and pain by depletion of neuropeptides like substance P in small sensory cutaneous nerves, has proven to be an effective and safe regimen resulting in clearing of the skin lesions. See Stander S., et al., *J Am Acad Dermatol:* 44, 471 (2001). Studies of the itch response in NC/Nga mice using capsaicin treatment showed that the spontaneous development of dermatitis lesions was almost completely prevented. Furthermore, the elevation of serum IgE levels was significantly suppressed and infiltrating eosinophils and mast cell numbers in lesional skin of capsaicin treated mice were reduced. See Mihara K., et al., *Br J Dermatol:* 151, 335 (2004). The observations from this group suggest that scratching behaviour might contribute to the development of dermatitis by enhancing various immunological responses, therefore implying that prevention of the itch sensation and/or itch-associated scratching behaviour might be an effective treatment for AD. See Mihara K., et al., *Br J Dermatol:* 151, 335 (2004).

Chronic delivery of IL-31 induces pruritis and alopecia in mice followed by the development of skin lesions resembling dermatitis suggesting that IL-31 induces itching. See See Dillon S. R., et al., *Nat Immunol:* 5, 752 (2004). Neutralization of IL-31 in IL-31 treated mice to prevent pruritis and alopecia was tested in Example 10. Neutralization of IL-31 may improve clinical outcome of prurigo nodularis. An IL-31 neutralizing antagonist could be effective in inhibiting, reducing, minimizing or preventing prurigo nodularis.

Skin-Tropic Viruses and Viral Associated Pruritis

Herpes Simplex Virus (HSV)-specific CD8+ T cells in the peripheral blood and HSV-specific CD8+ T cells recovered from herpes lesions express high levels of CLA whereas non-skin-tropic herpes virus-specific CD8+ T cells lack CLA expression. See Koelle D. M., et al., *J Clin Invest:* 110, 537 (2002). HSV-2 reactive CD4+ T lymphocytes also express CLA, but at levels lower than those previously observed for CD8+ T lymphocytes. See Gonzalez J. C., et al., *J Infect Dis:* 191, 243 (2005). Pruritis has also been associated with herpes viral infections (See Hung K. Y., et al., *Blood Purif:* 16, 147 (1998), though other viral diseases, like HIV, have also been associated with pruritic skin lesions. Severe, intractable pruritus, often associated with erythematopapular skin lesions and hypereosinophilia, is a condition observed in some nonatopic, HIV-infected patients 36. See Singh F. & Rudikoff D, *Am J Clin Dermatol;* 4, 177 (2003); and Milazzo F., Piconi S., et al., *Allergy:* 54, 266 (1999).

The association of skin-tropic viruses with pruritis and CLA+ T cells suggests that IL-31 producing T cells may be involved in the pathophysiology of viral infections. Thus, an IL-31 neutralizing antagonist could be effective in inhibiting, reducing, minimizing or preventing viarl associated pruritis, and neutralization of IL-31 may improve clinical outcome of viral associated pruritis.

IL-31 has been shown to induce several chemokine and cytokine genes in normal human epidermal ketatinocytes (NHEKs), including genes encoding GROα, (CXCL1), TARC (CCl17), MIP3β, (CCL19), MDC (CCL22), MIP-3 (CCL23), MIP-1β (CCL4), and I-309. See Dillon S. R., et al., *Nat Immunol:* 5, 752 (2004). TARC and MDC bind CCR4, a chemokine receptor associated with Th2-type T cells and predominantly expressed by CLA+ T cells in peripheral blood. Both chemokines have been implicated in the recruitment of T cells into the skin of AD patients suggesting that these chemokines contribute to the inflammatory process associated with the pathogenesis of AD. See Example 9 for a model to measure the reduction in TARC and MDC levels in CLA+ T cell mediated disease by administering an IL-31 antagonist.

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-31RA polypeptides, soluble heterodimeric and multimeric receptor polypeptides, or anti-IL-31 antibodies or binding partners of the present invention, and the like, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

Using methods known in the art, and disclosed herein, one of skill could readily detect IL-31 in diseases that have a high correlation of CLA+ T cells. Such methods involve taking a biological sample from a patient, such as blood, saliva, or biopsy, and comparing it to a normal control sample. Histological, cytological, flow cytometric, biochemical and other methods can be used to determine the relative levels or localization of IL-31, or cells expressing IL-31, i.e., monocytes, in the patient sample compared to the normal control. A change in the level (increase or decrease) of IL-31 expression, or a change in number or localization of monocytes (e.g., increase or infiltration of monocytic cells in tissues where they are not normally present) compared to a control would be indicative of disease. Such diagnostic methods can also include measuring TARC and MDC, for example. Such methods are well known in the art and disclosed herein.

IL-31 polypeptides that bind IL-31RA receptor polypeptides, and antibodies thereto are useful to antagonize or block signaling via IL-31RA-comprising receptors in the treatment of atopic dermatitis, contact dermatitis, drug induced delayed type cutaneous allergic reactions, toxic epidermal necrolysis, cutaneous T cell lymphoma, bullous pemphigoid, alopecia areata, vitiligo, acne rosacea, prurigo nodularis, and Herpes simplex virus.

IL-31 may also be used within diagnostic systems for the detection of circulating levels of ligand, and in the detection of diseases that are mediated by CLA+ T cells. IL-31 may also be used within diagnostic systems for the detection of circulating levels of ligand, and in the detection of diseases that have a high correlation of CLA+ T cells. Within a related embodiment, antibodies or other agents that specifically bind to IL-31 can be used to detect circulating IL-31 polypeptides; conversely, IL-31 itself can be used to detect circulating or locally-acting receptor polypeptides. Elevated or depressed levels of ligand or receptor polypeptides may be indicative of pathological conditions, including inflammation and pruritis.

Generally, the dosage of administered IL-31 antibody will vary depending upon such factors as the patient's age, weight, height, sex, general medical condition and previous medical history. One skilled in the art can readily determine such dosages, and adjustments thereto, using methods known in the art.

Administration of an anti-IL-31 antibody to a subject can be topical, intradermal, as an inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-31 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having IL-31 binding activity (Potts et al., *Pharm. Biotechnol.* 10:213 (1997)).

A pharmaceutical composition comprising a protein, polypeptide, or peptide having IL-31 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, molecules having IL-31 binding activity and a pharmaceutically acceptable carrier are administered to a patient in a therapeutically effective amount. A combination of a protein, polypeptide, or peptide having IL-31 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response. Similarly, an agent used to treat itching and pruritus associated with a disease mediated CLA+ T cells, or a disease with a high correlation of CLA+ Tcells, is physiologically significant if its presence alleviates at least a portion of the pruritic or itch response.

A pharmaceutical composition comprising an IL-31 antibody can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Polypeptides having IL-31 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

The invention is further illustrated by the following non-limiting examples.

EXAMPLES

Example 1

Determination of Human Primary T Cell Types that Express IL-31 Upon Stimulation

A. Selection of Study Subjects and Biopsies

Twelve patients with AD (moderate to severe disease; median age was 32 years old with skin involvement of 5-45%), 6 patients with psoriasis (median age was 56 years old with skin involvement of 10-65%) and 12 healthy individuals (median age 34 years) were included in A study after informed consent. None of the patients had received any systemic corticosteroids previously. All patients were off topical corticosteroids for one week before their skin biopsy or blood drawing. Two mm punch biopsies were taken from 1) acute erythematous AD lesions of less than three days' onset, 2) chronic, lichenified AD lesions of greater than two weeks' duration, 3) chronic psoriasis lesions, and 4) normal skin. The skin samples were immediately frozen at −70° C. for immunohistochemistry or Western and immuno-dot blotting.

B. Isolation and activation of primary human T cell subsets:

To isolate various T cell subsets, human PBMCs from the donors were isolated using standard Ficoll gradient centrifugation. Total T cells were then isolated using the T Cell Isolation Kit II (Miltenyi Biotec) according to the manufacturer's instructions. Separation efficiency was assessed using standard flow cytometry and determined to be >95% T cells. To separate CD45RA+ "naïve" T cells from the CD45RO+ "memory" T cells, the total T cell population was incubated with anti-CD45RO microbeads (Miltenyi Biotec) for 15 minutes at +4° C. and magnetically separated according to the manufacturers instructions. The naïve and memory T cell populations were determined to be >90% pure by flow cytometry.

CD45RO+ memory T cells are often tissue specific and cutaneous lymphocyte antigen (CLA) is used to differentiate skin-homing T cells from gut-homing T cells expressing α4/β7 on their surface. To determine which of these cell types produce IL-31, CLA+ T cells were isolated from total T cells, activated and conditioned media was collected for the IL-31 bioassay. To do this, total T cells were isolated and then incubated on ice for 20 minutes in 1 mL of a 1:50 dilution of anti-CLA-FITC antibody (PharMingen). Cells were then washed, resuspended in MACS buffer and incubated with anti-FITC microbeads (Miltenyi Biotec) for 15 minutes at +4° C. The cells were then washed, resuspended and magnetically separated over an LS column according to the manufacturers instructions. The labeled T cells were later determined to be >80% pure while the CLA-depleted T cells were >98% CLA−. Both CLA+ and CLA− T cells were collected and cultured concurrently.

To activate the CD45RA+ and CD45RO+ T cell subsets, cells were cultured overnight in 24-well tissue culture plates pretreated with 2.0 μg/mL anti-CD3 antibody (Southern Biotechnology). The cells were plated at a concentration of $2.5 \times 10^6$ cells/mL in tissue culture media (RPMI, 5% fetal bovine serum, L-Glutamine and Sodium Pyruvate (all Gibco)) supplemented with 2.0 μg/mL anti-CD28 (Southern Biotechnology) and placed in a +37° C. incubator. After four hours, half of the wells were harvested, cells pelleted and conditioned media frozen at −20° C. until time of IL-31 bioassay.

The CLA+ and CLA− T cell subsets were activated similarly in 48-well tissue culture plates that were pretreated with 2.0 μg/mL anti-CD3 antibody (Southern Biotechnology). The cells were activated for 16 hours or 24 hours in a +37° C. incubator at a concentration of $6.25 \times 10^5$ cells/mL. Samples were harvested, cells pelleted and conditioned media frozen at −20° C. until time of IL-31 bioassay. For suboptimal activation, CLA+ T cells were cultured in plates pre-treated with 0.5 ug/ml of anti-CD3 antibody.

C. Human IL-31 Bioassay Protocol:

BAF3 cells transfected with hIL-31RA, hOSMRB, and KZ134 (a signal transducer and activator of transcription-activated luciferase reporter) were grown to $5 \times 10^5$ and $1 \times 10^6$ cells/mL. Cells were washed with assay media (RPMI 1640, 10% FBS, L-Glutamine, Sodium Pyruvate, and Pen/Strep (all Gibco)) and resuspended at $3 \times 10^5$ cell/mL in assay medium. In a 96-well opaque plate, μL-31 standards were titered in duplicate from 600 pg/mL to 9.38 pg/mL in assay medium via a 100 μL/well, 1:2 serial dilution. Quality control standards were added in duplicate to the plate at 350 pg/mL and 35 pg/mL in 100 μL. Test samples were often diluted 1:2 or 1:4 and added in duplicate to the sample wells. 100 μL of the washed BAF3 cells were then added to each well for a final concentration of $3 \times 10^4$ cells/well. The plate was then incubated for 16-24 hours at +37° C. in a 5% $CO_2$ incubator. The plate was then centrifuged at 1200 RPM for 5 minutes, media flicked off and 25 μL/well of lysis buffer (Promega) added to each well. After 10 minutes the plate was read on a luminometer (Berthold). The luminometer added 40 μL/well of luciferase substrate mix (Promega) and integrated the luminescence for a period of 4 seconds. Luminescence values were exported to a spreadsheet where they were analyzed and converted into picograms of IL-31 per $10^6$ cells per mL of volume. The data is summarized in Table 1.

D. Results of IL-31 Bioassay:

The results from the CD45RA+ and the CD45RO+ T cell samples revealed that IL-31 was primarily produced by activated CD45RO+ memory T cells. The CD45RA+ and CD45RO+ T cells from both donors produced no detectable IL-31 when unstimulated. However, the CD45RO+ samples from both donors #3 and #4 generated significant levels of IL-31 following a 24 hour activation with plate-bound anti-CD3 and soluble anti-CD28 (110.4 pg/$10^6$ cells/mL and 145.6 pg/$10^6$ cells/mL respectively). Conversely, when the CD45RA+ T cells from donors #3 and #4 were activated with anti-CD3 and anti-CD28, they produced very low amounts of IL-31 (13.1 pg/$10^6$ cells/mL and 12.7 pg/$10^6$ cells/mL respectively).

The CLA+ and CLA− T cell samples revealed that IL-31 seems to be made almost entirely by activated CLA+ T cells. The CLA− population of T cells (which includes naïve T cells, α4/β7 gut-homing memory T cells, and tissue uncommitted T cells) from both donors generated no detectable levels of IL-31 regardless of time point or activation condition. The CLA+ T cells on the other hand, generated very high levels of IL-31 when stimulated with 2.0 μg/mL plate-bound anti-CD3 antibody. Donor #5 generated 1385.7 pg/$10^6$ cells/mL IL-31 by 16 hours and >1920 pg/$10^6$ cells/mL by 24 hours. Donor #6 generated 121.3 pg/$10^6$ cells/mL IL-31 at 16 hours and 328.9 pg/$10^6$ cells/mL IL-31 at 24 hours. These results clearly demonstrate that of the T cell subsets, IL-31 seems to be made specifically by cutaneous (CLA+) T cells under standard activation conditions.

TABLE 1

| Donor# | Cell Type | Activation | IL-31 (pg/$10^6$ cells/mL) | IL-31 (pg/$10^6$ cells/mL) |
|---|---|---|---|---|
| | | | 6 hr | 24 hr |
| 3 | CD45RA+ | αCD3+ αCD28 | Below Detection | 13.1 |
| 3 | CD45RO+ | αCD3+ αCD28 | 8.6 | 110.4 |
| 4 | CD45RA+ | αCD3+ αCD28 | 6.7 | 12.7 |
| 4 | CD45RO+ | αCD3+ αCD28 | 11.9 | 145.6 |
| | | | 16 hr | 24 hr |
| 5 | CLA+ T Cells | Unstimulated | Below Detection | Below Detection |
| 5 | CLA+ T Cells | αCD3 | 1385.7 | >1920 |
| 5 | CLA− T Cells | Unstimulated | Below Detection | Below Detection |
| 5 | CLA− T Cells | αCD3 | Below Detection | Below Detection |

TABLE 1-continued

| Donor# | Cell Type | Activation | IL-31 (pg/10$^6$ cells/mL) | IL-31 (pg/10$^6$ cells/mL) |
|---|---|---|---|---|
| 6 | CLA+ T Cells | Unstimulated | Below Detection | Below Detection |
| 6 | CLA+ T Cells | αCD3 | 121.3 | 328.9 |
| 6 | CLA− T Cells | Unstimulated | Below Detection | Below Detection |
| 6 | CLA− T Cells | αCD3 | Below Detection | Below Detection |

Example 2

IL-31 Involvement in Initiation and Perpetuation of Contact Hyper-Sensitivity

A. Method I

BALB/c mice are painted on shaved mid-back with 25 ul of 0.5% DNFB dissolved (2,4, dinitro-fluoro-benzene, Sigma, St. Louis Mo.) in acetone:olive oil (4:1) solution using a pipettor. A vehicle control group receives 25 ul of acetone:olive oil only. After 5 days, mice are anaesthetized with isofluorane in an inhalation chamber and both ear pinnae of experimental and control animals are measured with an engineer's micrometer (Mitutoyo) to obtain a baseline measurement. Mice are then challenged by applying 10 ul of 0.25% DNFB in acetone:olive oil (4:1) to both sides of each ear of all mice. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice.

Whole blood and serum for FACS and/or ELISA analysis are collected prior to sacrifice and ears are collected for histology.

Method II (Induces Th2 Responses)

BALB/c mice are painted on shaved mid-back with 100 ul of 0.5% FITC (fluorescein isothiocyanate) in a 1:1 solution of acetone/dibutyl phthalate (MSDS available using pipettor on days 1, 2 and 8. On day 13, mice are anaesthetized with isofluorane in an inhalation chamber and both ear pinnae of experimental and control animals are measured with an engineer's micrometer (Mitutoyo) to obtain a baseline measurement. Mice are challenged by applying 25 ul of 0.5% FITC (in 1:1 acetone/dibutyl phthalate) to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Method III (Induces Th1 Responses)

BALB/c mice are painted on shaved mid-back with 25 ul of 2% oxazalone (in 4:1 acetone/olive oil) using pipettor. On day 7, mice are anaesthetized with isofluorane in an inhalation chamber and both ear pinnae of experimental and control animals are measured with an engineer's micrometer (Mitutoyo) to obtain a baseline measurement. Mice are challenged by applying 8 ul of oxazalone to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Involvement of IL-31 in the initiation and perpetuation of contact hyper-sensitivity is tested using a neutralizing antibody against IL-31 both at the sensitization and challenge phases of the experiment.

Example 3

IL-31 Involvement in Atopic Dermatitis

A. Methods I (Sensitization of NC/Nga Mice)

Male NC/Nga mice were purchased from Charles River Laboratories, Japan. The mice were 4 weeks old on arrival and housed in SPF quarantine conditions for 4 weeks to acclimate. The mice were approximately 10-11 weeks old at the start of the antigen sensitization. Mice were anaesthetized with isofluorane and backs were shaved with electric clippers. Approximately 10 ug of *Dermatophagoides pteronyssinus* (Dp) (Indoor Biotechnologies, Charlottesville, Va., special order) extract was injected intradermally at the nape of the neck 3 times per week for 5 to 6 weeks until mice developed skin lesions. Control animals received 10 ul PBS intradermal injections 3 times per week. The Dp extract was prepared according to method by Matsuoka and colleagues. Matsuoka H., et al., *Allergy:* 58, 139 (2003). Briefly, 595 mg Dp lyophilized spent culture extract was dissolved in 12 mL sterile PBS (Gibco). Dp was mixed in a 50 mL Falcon tube on a shaking rocker for 30 minutes. The extract was spun for 10 minutes at 2000 rpm and the supernatant was collected and aliquoted into 1 mL cryovial tubes and stored at −20° C.

B. Method II (Sensitization of DO11.10 Mice)

DO11.10 transgenic mice were bred from an in-house colony and were between 9.5 and 14 weeks old at start of antigen sensitization. 24 hours prior to epicutaneous sensitization mice were anaesthetized with isofluorane and the entire trunk (back and abdomen) of mice were shaved with electric clippers. The mice were then tape stripped with Elastin surgical tape (Johnson and Johnson) on the back. 1 cm2 sterile gauze patches were wetted with either 500 ug ovalbumin (Calbiochem 32467) or sterile PBS (Gibco) and adhered to left backside of mice with DuoDerm Extra Thin Dressing (ConvaTec 187932). The patch and dressing were then covered in a body wrap of the Elastin surgical tape so mice could not remove or destroy the patches. Patches were worn for 7 days and removed. The mice were rested for two weeks before having another round of epicutaneous sensitization. Mice received a total of three one-week sensitizations.

Results:

Immunohistochemical analysis of IL-31RA expression in lesional and non-lesional skin from dust mite sensitized NC/Nga and OVA sensitized DO11.10 animals showed that IL-31RA is expressed by epidermal keratinocytes in mice, however no significant difference in levels of expression was found between antigen sensitized versus PBS sensitized animals in this study.

Example 4

IL-31 Involvement Delayed Type Hypersensitivity

A. Methods

To generate a DTH response, mice were sensitized to antigen on day 0 by subcutaneous immunization at the base of the tail with 100 ug ovalbumin (OVA) in complete Freund's adjuvant (CFA, 50-100 ul total volume). One week later mice were anesthetized with isofluorane in an inhalation chamber and both ear pinnae of experimental and control animals were measured with an engineer's micrometer (Mitutoyo) to obtain a baseline measurement. Mice were challenged intradermally with 10 ug OVA in PBS in a total volume of 10 ul into the left ear pinnae, just below the skin without hitting any veins. As a control, mice also received an injection of 10 ul PBS in the right ear pinnae. In some cases, a separate control group given an i.d. injection of OVA in the ear may also be treated with topical corticosteroids as a positive control to inhibit the reaction. At 24 and 48 hr after challenge, mice were anesthetized and ear thickness was measured. Results were expressed as: Specific ear swelling=(24 hr measurement–0 hr measurement) for experimental ear–(24 hr measurement–0 hr measurement) for negative control ear. Induration, the hallmark of DTH, is detectable by 18 hours after injection of sensitized antigen and is maximal by 24-48 hours. The lag in the onset of palpable induration is the reason for naming the response "delayed type."

B. Results

IL-31 transgenic mice were tested for DTH, however, due to an increase in ear thickness in un-challenged IL-31 transgenic animals, no statistically significant difference in DTH could be determined between IL-31 Tg animals compared to wildtype controls in this study. IL-31 receptor knockout animals were also tested in a DTH response and no significant difference in the DTH response could be observed between receptor knockout and wildtype animals.

Example 5

Immunohistochemical (IHC) Staining of IL-31 in Skin Lesions from Uninvolved Psoriatic, and Atopic Dermatitis Uninvolved psoriatic, atopic dermatitis and normal skin were tested for the IL-31 ligand by IHC. Positive control cells consisted of BHK cells transfected with IL-31. Negative controls performed included: (1) un-transfected BHK cells, (2) staining representative tissues and cells with protein A purified Normal Rabbit serum and detecting antibody binding as usual. Antibody reagent was E5758 (Rabbit anti-huIL-31 CEE, Aff. Purified at 1.0 mg/ml). Control cells included C02-6020: BHK cells expressing zcytor17 Lig hu-CEE/21, and a BHK wild type. Tissues tested included acute atopic dermatitis skin samples, chronic atopic dermatitis skin samples, unaffected area skin samples, and normal control skin samples and other in-house control samples.

The cells and tissues described above were fixed overnight in 10% NBF and embedded in paraffin using standard techniques.

5 µM sections were baked at 61° C. for 30 min for tissue adhesion. Slides were subsequently dewaxed in 3×5' in xylene and rehydrated through graded alcohols as follows: 2×2' in 100% EtOH, 2×2' in X95% EtOH, 1×2' in 70% EtOH. Slides were rinsed in dH20, and then heat induced epitope retrieval (HIER) was performed for 20 minutes under steam followed by 20 minutes cooling to RT in 10 mM Tris, 1 mM EDTA, pH 9.0

Slides were loaded onto a DakoCytomation Autostainer. Slides were rinsed with TBS/Tween buffer (TBST), prepared as recommend by manufacturer. Endogenous biotin was blocked with a 10 minute incubation in avidin solution, washed in TBST followed by a 10 minute incubation in biotin solution. Slides were washed in TBST. A protein block (PBSB) (0.5% Blocking Powder in PBS, Perkin Elmer NEL700001KT.) was applied for 30 minutes and rinsed off slides. The primary antibody was diluted to 500 ng/ml and was applied for 60 minutes in ChemMate Antibody Dilution Buffer (part#ADB250, Ventana Medical systems).

Tissues washed twice in TBST, and then incubated 45 minutes in biotinylated Goat anti-Rabbit Ab, 750 ng/ml in PBSB (catalog #BA-1000, Vector Labs). Slides washed twice in TBST. Vectastain Elite ABC Reagent (catalog#PK-7100, Vector Labs) was incubated for 45 minutes. Slides washed twice in TBST. Signals were developed with DAB+ (catalog#K-3468, DakoCytomation) for 10 minutes at room temperature. Tissue slides were then counterstained in hematoxylin (catalog#H-3401 Vector Labs), dehydrated and coverslipped in VectorMount (catalog#H-5000, Vector Labs).

Results:

1) Cell Controls:

BHK cells transfected with IL-31 was positively stained with IL-31 antibody E5758 while un-transfected cells was negative for this antibody. The same transfected and un-transfected cells were negative with anti-rabbit sera.

2) Atopic Dermatitis Skin Analysis:

The staining pattern for IL31 in the AD skin samples is identical to that of psoriasis skins reported previously: keratinocyte and CD3 positive T-cells stained negative for IL31. A weak but rather uniform staining of the epithelial cells in the secretory portion of the sweat glands was present, but a strong signal was observed in the inner layer of epithelium in the duct portion. Sebaceous gland was positive for IL31. There was no difference in the IL31 staining between AD and normal skin.

Immunohistochemical (IHC) staining of uninvolved psoriatic, atopic dermatitis and normal skin showed strong staining of IL-31 in the holocrine secretion of the sebaceous glands. Considering the phenotype of IL 31 transgenic mice, it is interesting to note that the sebaceous glands originate as an epithelial bud from the outer root sheath of hair follicles. In addition to sebaceous glands weak but rather uniform staining of IL-31 was observed in the epithelial cells in the secretory portion of the sweat glands and a strong signal in the inner layer of epithelium was observed in the duct portion of sweat glands.

Example 6

Immunohistochemical (IHC) Staining of IL-31RA in Uninvolved Psoriatic and Atopic Dermatitis Uninvolved psoriatic, atopic dermatitis and normal skin were tested for the IL-31RA by IHC. Positive control cells consisted of BHK cells dual transfected with IL-31RA and OSMR. Negative controls performed included: (1) un-transfected BHK cells, (2) staining representative tissues and cells with protein A purified Normal Rabbit serum and detecting antibody binding as usual. Antibody reagent was E6292 (Rabbit anti-huIL-31RAs-CEE v.4 at 1.33 mg/ml). Control cells included C02-5117 BHK cells expressing human IL-31RA and human OSMR (Total cells in the pellet: 3.9× 106, vitality was >90%) and C04-1587: BHK wild type (Total cells in the pellet: 5×106). Other tissues examined included: 5 Acute atopic dermatitis skin samples, 10 Chronic atopic dermatitis skin samples, 10 Unaffected area skin samples, Normal control skin samples, and other in-house skin samples.

The cells and tissues described above were fixed overnight in 10% NBF and embedded in paraffin using standard techniques.

5 μM sections were baked at 61° C. for 30 min for tissue adhesion. Slides were subsequently dewaxed in 3×5' in xylene and rehydrated through graded alcohols as follows: 2×2' in 100% EtOH, 2×2' in X95% EtOH, 1×2' in 70% EtOH. Slides were rinsed in dH20, and then heat induced epitope retrieval (HIER) was performed for 20 minutes under steam followed by 20 minutes cooling to RT in 10 mM Tris, 1 mM EDTA, pH 9.0

Slides were loaded onto a DakoCytomation Autostainer. Slides were rinsed with TBS/Tween buffer (TBST), prepared as recommend by manufacturer. Endogenous biotin was blocked with a 10-minute incubation in avidin solution, washed in TBST followed by a 10-minute incubation in biotin solution. Slides were washed in TBST. A protein block (PBSB) (0.5% Blocking Powder in PBS, Perkin Elmer NEL700001KT.) was applied for 30 minutes and rinsed off slides. Primary antibodies diluted from 665 ng/ml to 1330 ng/ml for IL31RA were applied for 60 minutes in ChemMate Antibody Dilution Buffer (part#ADB250, Ventana Medical systems).

Tissues were washed twice in TBST, and then incubated 45 minutes in biotinylated Goat anti-Rabbit Ab, 750 ng/ml in PBSB (catalog #BA-1000, Vector Labs). Slides were washed twice in TBST. Vectastain Elite ABC Reagent (catalog#PK-7100, Vector Labs) was incubated for 45 minutes. Slides were washed twice in TBST. Signals were developed with DAB+ (catalog#K-3468, DakoCytomation) for 10 minutes at room temperature. Tissue slides were then counterstained in hematoxylin (catalog#H-3401 Vector Labs), dehydrated and coverslipped in VectorMount (catalog#H-5000, Vector Labs).

Results are shown in Table 2.

TABLE 2

Results of IHC for IL-31RA in skin biopsy specimens from patients with involved and uninvolved AD compared to healthy volunteers

| CASE ID | IL-31RA IHC SCORE* | CD3 IHC SCORE* |
|---|---|---|
| AD-1 | 2-3 | 0-1 |
| AD-2 | 2-3 | 2 |
| AD-3 | 2-3 | 1-2 |
| AD-4 | 3 | 1 |
| AD-5 | 2 | 2 |
| UAD-1 | 1-2 | 1 |
| UAD-2 | 1 | 0-1 |
| UAD-5 | 1-2 | 0-1 |
| UAD-6 | 2-3 | ND |
| UAD-7 | 2 | 1 |
| UAD-8 | 1 | 1 |
| UAD-9 | 1-2 | 1 |
| UAD-10 | 2 | ND |
| Normal-1 | 1 | 0-1 |
| Normal-2 | 0-1 | 0-1 |
| Normal-3 | 1 | 0-1 |

Abbreviations:
AD: atopic dermatitis;
UAD: uninvolved AD;
ND: Not Done
*IHC signal was scored from 0 (no signal) to 4 (intense signal)

There was a slight up regulation of IL31RA in the epidermis of AD skin samples. Possibly a small percentage of CD3 positive T-cells were positive for IL31RA in the AD skins. There were CLA positive cells in all skin samples tested. AD skins may have more CLA positive cells than that of the normal or UAD samples.

The receptor for IL-31, IL-31RA was also expressed in the epithelial cells of eccrine sweat glands with the cuboidal epithelial cells in the secretory portion of the eccrine glands demonstrating slightly higher level of IL-31RA protein compared to the duct portion.

Collectively, these data demonstrate that IL-31RA is expressed by epidermal keratinocytes from both control volunteers and AD patients. However, the levels of IL-31RA expressed on keratinocytes from AD skin biopsies were higher than the levels observed in skin biopsies from normal controls, indicating a potential for increased responsiveness to IL-31 in the context of AD.

IL-31RA was also found expressed on a subset of perivascular infiltrating cells present in skin biopsies from AD patients but was not present in control skin biopsies. These IL-31RA+ cells were recognized by an antibody specific for the tissue macrophage marker CD68, indicating these cells were skin-infiltrating tissue macrophages.

Example 7

Isolation of Skin Infiltrating Cells by Laser Capture Microscopy and Analysis of IL-31 mRNA by RT-PCR The presence of skin infiltrating T cells is a distinguishing feature in skin biopsies from AD patients compared to normal individuals. Since IL-31 is a T cell associated cytokine, the expression of IL-31 in skin-infiltrating T cells in tissue biopsies from AD patients was examined. First, the presence of increased numbers of CD3+ T cells in skin tissue biopsies from AD patients compared to normal individuals was confirmed by IHC. See Table 2. Next, laser capture microscopy was used to specifically isolate skin infiltrating cells for analysis of IL-31 mRNA by RT-PCR. IL-31 mRNA was expressed by skin infiltrating cells from acute AD patients. In normal tissues, infiltrating cells are not normally found and therefore could not be tested. However, the epidermal keratinocyte layer, which is present in both AD and normal skin, was analyzed for IL-31 mRNA expression and lower levels of IL-31 mRNA were found in normal samples compared to the epidermal keratinocyte layer of AD samples. Semi-quantitative analysis of IL-31 mRNA expression compared to an internal control gene (HPRT) showed that although IL-31 mRNA levels were not significantly different between AD and normal samples, there was a trend towards higher IL-31 expression in skin from AD patients.

Example 8

IL-31 is Produced by Memory T Cells with a Skin-Homing Phenotype

Analysis of skin biopsies confirmed that the infiltrating CD3+ T cells in the skin, which express IL-31 mRNA, express the skin-homing marker cutaneous lymphocyte antigen (CLA). Of the total T cell population in normal human peripheral blood, IL-31 expression was found to be largely restricted to CD45RO+ memory/effector cells as opposed to the CD45RA+ naïve T cell population.

In order to determine if IL-31 production was associated with CLA+ skin-homing T cells, CLA+ and CLA− T cells were isolated from peripheral blood of patients diagnosed with AD and control volunteers and compared IL-31 mRNA and protein levels following anti-CD3 plus anti-CD28 stimulation. Our results indicate that IL-31 mRNA was significantly elevated in CLA+ T cells from both AD and normal individuals at both 4 h (p0.0087 and p0.0022 CLA+ compared to CLA− for AD and normal, respectively) and 24 h (p0.0022 CLA+ compared to CLA− for both AD and normal samples) post stimulation. Analysis of IL-31 protein levels in culture supernatants confirmed that IL-31 was produced predominantly by CLA+ T cells as there was no detectible IL-31 in culture supernatants from CLA− T cells from both AD and control individuals. There were no significant differences in IL-31 levels between AD and normal patients. We also analysed the production of IL-31 by peripheral blood T cells that express other tissue-specific homing markers, such as the gut-specific homing marker $\alpha 4\beta 7$, from normal volunteers. Comparison of the IL-31 levels produced by CLA+ T cells and $\alpha 4\beta 7+$ cells demonstrated CLA+ T cells preferentially produce IL-31 compared to the $\alpha 4\beta 7+$ cells (average of 34.5 pg/ml and 14.42 pg/ml IL-31, respectively).

Although both AD patients and normal controls have circulating CLA+ T cells that express IL-31 upon activation, CLA+ T cells from AD patients are reported to exist in a more activated state compared to cells from normal individuals. Consequently, the threshold of stimulation required for the production of IL-31 by CLA+ T cells may differ between dermatitis patients and control subjects. To test this hypothesis, we stimulated CLA+ T cells from AD patients and control individuals with sub-optimal concentrations of anti-CD3 in the absence of anti-CD28 and analyzed the production of IL-31 in culture supernatants at 24 h after stimulation. Our results demonstrate that circulating CLA+ T cells from some AD patients produce higher levels of IL-31 compared to cells from normal individuals in this study with maximum levels reaching 1200 pg/mL, whereas maximal detected levels in normal CLA+ supernatants was only 400 pg/ml and maximal detected levels for psorasis patients was 73 pg/ml at suboptimal concentrations of anti-CD3 stimulation. Five of eleven AD patients showed IL-31 levels below the limit of detection of our assay suggesting there might be a subset of AD patients where IL-31 is produced at low levels. This may reflect variations in the stage of disease of our study population. Nevertheless, more than half of the AD patients showed a trend towards higher IL-31 levels compared to psoriasis patients and normal individuals following suboptimal stimulation with anti-CD3. Since more CLA+ T cells are localized in skin of AD patients as compared to normal individuals, our studies suggest that there is an increased potential for IL-31 activity in the AD skin micro-environment. Thus, this study may suggest a subpopulation of AD patients, which have more activated CLA+ T cells producing IL-31.

Example 9

Reduction of TARC and MDC in Response to Anti-Il-31 Antibody in AD Mouse Models Method I Six-week old male NC/Nga mice (CRL Japan) were sensitized intradermally with 50 µg dust mite extract (D. pteronyssinus, Indoor Biotechnologies) three times a week on the back and scored for AD-like lesions. After 5 weeks of sensitization the mice were euthanized and the right ears were excised and placed into a single well of a 48-well culture dish (Corning) supplemented with RPMI+2% FBS (GIBCO Invitrogen). Plates were placed in 5% CO2 humidity controlled incubators. Supernatants were collected after 24 hours and frozen at −20° C. until further analysis.

Method II

Twelve-week old female NC/Nga mice (CRL Japan) were sensitized intradermally with 10 µg SEB (Toxin Technology) in the ear and on the back three times per week. The mice were scored for AD-like lesions. After 5 weeks of sensitization the mice were euthanized and 6 mm biopsy punches were taken from the injected ear of each mouse and placed into a single well of a 48-well culture dish supplemented with RPMI+2% FBS. Plates were placed in 5% CO2 humidity controlled incubators. Supernatants were collected after 24 hours and frozen at −20° C. until further analysis.

Groups of mice in both studies were treated with either a rat anti-mouse IL-31 monoclonal antibody at 10 mg/kg or vehicle, intraperitoneally two times each week starting after 1 to 2 weeks of sensitization.

TARC and MDC concentrations in the 24-hour supernatant samples were measured by conventional ELISA (R&D Systems).

TARC and MDC concentrations were lower in ear supernatants from anti-IL-31 treated mice compared to control mice in both studies, however, these results were not statistically significant when analyzed by ANOVA, probably due to small sample size. When the data from both experiments is combined and analyzed there is a statistically significant difference between treated groups.

Example 10

Administration of IL-31 Neutralizing Antibody

Normal female BALB/c mice (CRL) approximately 8 to 12 weeks old were implanted subcutaneously with 14-day osmotic pumps (Alzet, #2002) delivering 1 ug/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/0.1% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-m/L-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 can delay the onset of the scratch/hairloss response induced by IL-31.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of predicting the therapeutic response to an IL-31 antibody in an individual with atopic dermatitis comprising the steps of:
   a. obtaining a blood sample from the individual;
   b. obtaining a blood sample from a control;
   c. isolating circulating cutaneous lymphocyte positive T cells from the samples;
   d. activating the isolated cells with 0.5 ug/ml of anti-CD3 antibody;
   e. detecting IL-31 production from the isolated cutaneous lymphocyte positive T cells; and
   f. correlating a greater amount of IL-31 production in the individual versus the control with a therapeutic response to the IL-31 antibody.

2. The method of claim 1, wherein said detecting step further comprises detecting IL-31 production with a cell transfected with human IL-31RA and human OSMRB.

3. The method of claim 2, wherein the detection of IL-31 production is measured in picograms of IL-31 per $10^6$ cells per milliliter.

4. The method of claim 1, wherein the detecting step uses a luminometer.

* * * * *